(12) United States Patent
Sgroi, Jr. et al.

(10) Patent No.: US 10,667,408 B2
(45) Date of Patent: May 26, 2020

(54) FULLY ENCAPSULATED ELECTRONICS AND PRINTED CIRCUIT BOARDS

(71) Applicant: Covidien LP, Mansfield, MA (US)

(72) Inventors: Anthony Sgroi, Jr., Wallingford, CT (US); Patrick Mozdzierz, Glastonbury, CT (US); Stephen Paul, East Hartford, CT (US); David Valentine, Hamden, CT (US); Scott Firth, Guilford, CT (US)

(73) Assignee: COVIDIEN LP, Mansfield, MA (US)

( * ) Notice: Subject to any disclaimer, the term of this patent is extended or adjusted under 35 U.S.C. 154(b) by 0 days.

(21) Appl. No.: 16/270,721

(22) Filed: Feb. 8, 2019

(65) Prior Publication Data

US 2019/0174636 A1 Jun. 6, 2019

Related U.S. Application Data

(63) Continuation-in-part of application No. 15/947,314, filed on Apr. 6, 2018.

(Continued)

(51) Int. Cl.
*H05K 3/28* (2006.01)
*H05K 5/00* (2006.01)
(Continued)

(52) U.S. Cl.
CPC ....... *H05K 3/284* (2013.01); *A61B 17/07207* (2013.01); *A61B 17/1155* (2013.01); *B29C 45/14549* (2013.01); *B29C 45/14639* (2013.01); *B29C 45/14836* (2013.01); *H01R 12/62* (2013.01); *H05K 1/0281* (2013.01); *H05K 5/0026* (2013.01); *H05K 5/062* (2013.01); *A61B 2017/00017* (2013.01); *A61B 2017/0046* (2013.01); *A61B 2017/00398* (2013.01);

(Continued)

(58) Field of Classification Search
CPC ...... H05K 5/0095; H05K 5/0091; H05K 3/28; H05K 3/281; H05K 3/282; H05K 3/284; H05K 3/285; H05K 3/287; H05K 3/288
See application file for complete search history.

(56) References Cited

U.S. PATENT DOCUMENTS 4,372,037 A 2/1983 Scapple et al.
4,420,652 A 12/1983 Ikeno
(Continued)

FOREIGN PATENT DOCUMENTS

DE 3913066 A1 11/1990
WO 2009021827 A2 2/2009

OTHER PUBLICATIONS

Extended European Search Report corresponding to counterpart Patent Appln. EP 18 17 3035.9 dated Oct. 15, 2018.

*Primary Examiner* — Jeremy C Norris

(57) ABSTRACT

A method of encapsulating and hermetically sealing a printed circuit board of a flex cable includes: positioning a printed circuit board portion of a flex cable into a channel defined in a first mold half of a mold, the printed circuit board portion including a substrate and electronic components mounted on the substrate; mounting a second mold half onto the first mold half to enclose the channel of the first mold half and form a cavity within the mold; and filling the cavity of the mold with an encapsulation material through an inlet opening defined through the mold.

19 Claims, 14 Drawing Sheets

Related U.S. Application Data

(60) Provisional application No. 62/508,101, filed on May 18, 2017.

(51) Int. Cl.
  *H05K 1/02* (2006.01)
  *H01R 12/62* (2011.01)
  *B29C 45/14* (2006.01)
  *A61B 17/115* (2006.01)
  *H05K 5/06* (2006.01)
  *A61B 17/072* (2006.01)
  *B29L 31/34* (2006.01)
  *A61B 17/00* (2006.01)
  *A61B 90/00* (2016.01)

(52) U.S. Cl.
  CPC ........... *A61B 2017/00473* (2013.01); *A61B 2017/00526* (2013.01); *A61B 2017/00734* (2013.01); *A61B 2090/064* (2016.02); *A61B 2090/0813* (2016.02); *B29C 45/14065* (2013.01); *B29C 2045/14844* (2013.01); *B29L 2031/3481* (2013.01); *H05K 2203/1316* (2013.01)

(56) References Cited

U.S. PATENT DOCUMENTS

| | | |
|---|---|---|
| 4,672,418 A | 6/1987 | Moran et al. |
| 5,041,943 A | 8/1991 | Ilardi et al. |
| 5,223,741 A | 6/1993 | Bechtel et al. |
| 5,280,413 A | 1/1994 | Pai |
| 5,497,290 A | 3/1996 | Fukui et al. |
| 5,940,279 A | 8/1999 | Gademann et al. |
| 6,320,128 B1 | 11/2001 | Glovatsky et al. |
| 6,351,194 B2 | 2/2002 | Takahashi et al. |
| 6,449,168 B1 | 9/2002 | Soderholm |
| 7,898,074 B2 | 3/2011 | Eckhardt et al. |
| 8,354,587 B2 | 1/2013 | Tappel et al. |
| 8,666,505 B2 | 3/2014 | O'Brien et al. |
| 8,756,801 B2 * | 6/2014 | Nall ............... F21V 29/004 29/841 |
| 9,442,131 B2 | 9/2016 | Hazel et al. |
| 2008/0128886 A1 | 6/2008 | Kang et al. |
| 2013/0070427 A1 | 3/2013 | Tzu |
| 2016/0296234 A1 | 10/2016 | Richard et al. |
| 2016/0310134 A1 | 10/2016 | Contini et al. |
| 2018/0242970 A1 | 8/2018 | Mozdzierz |

\* cited by examiner

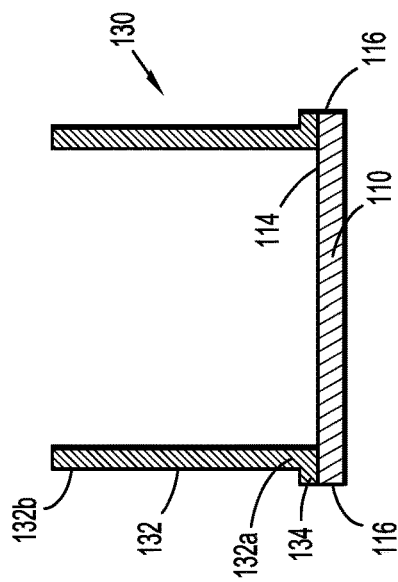
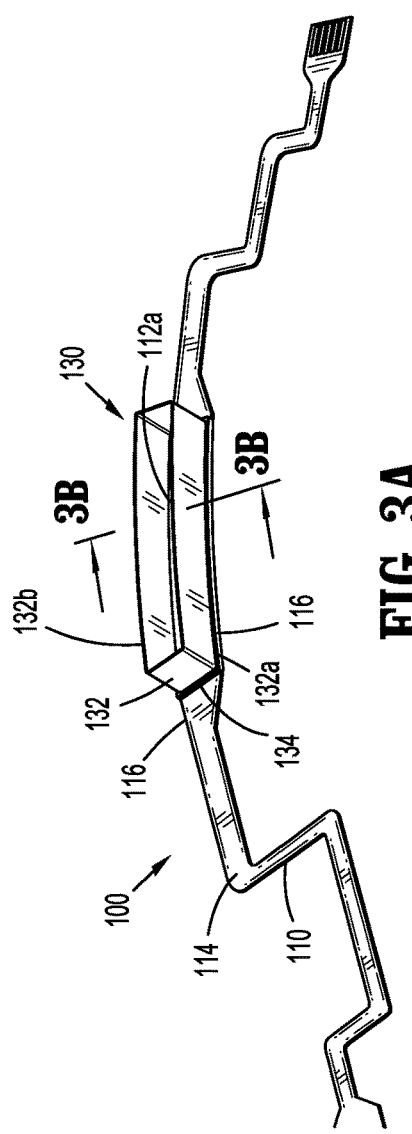
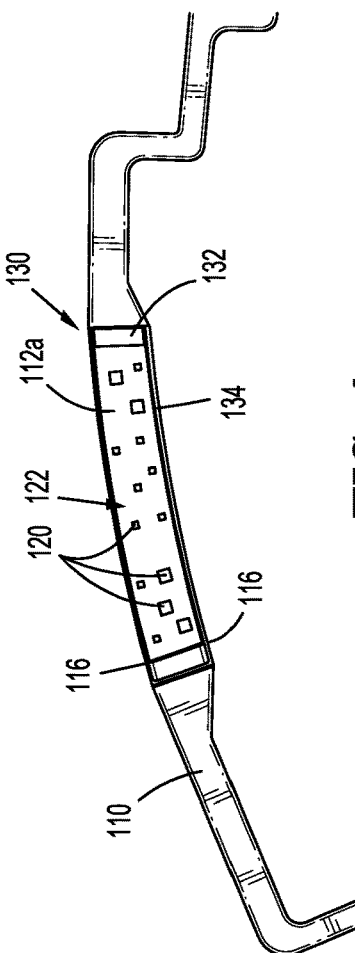
FIG. 3B
FIG. 3A
FIG. 4

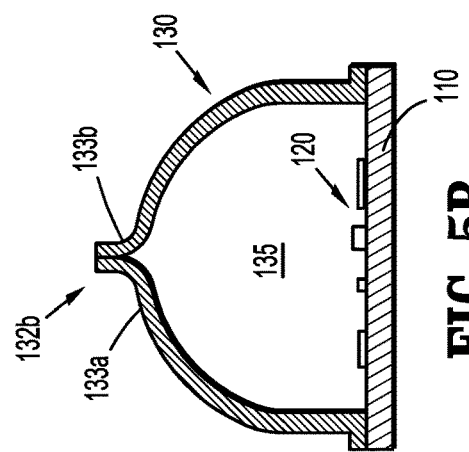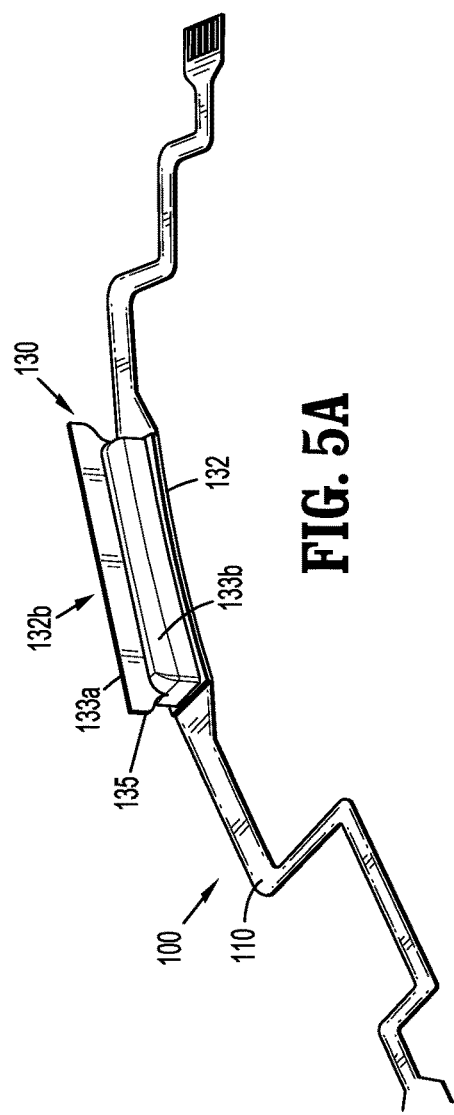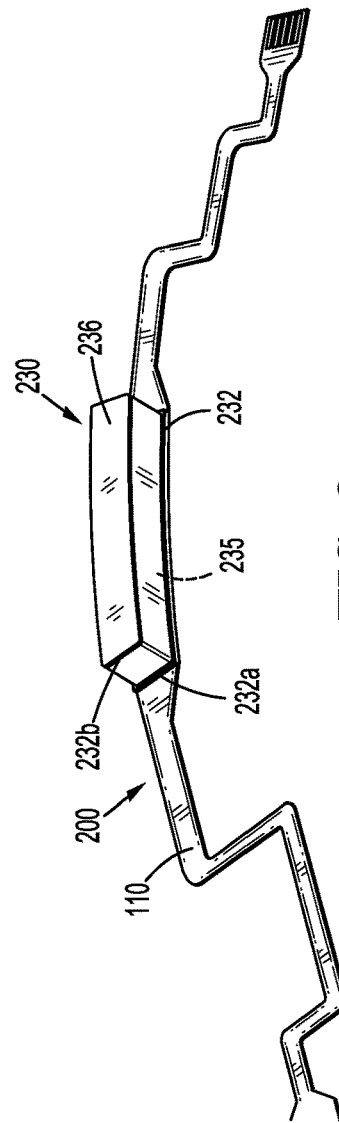

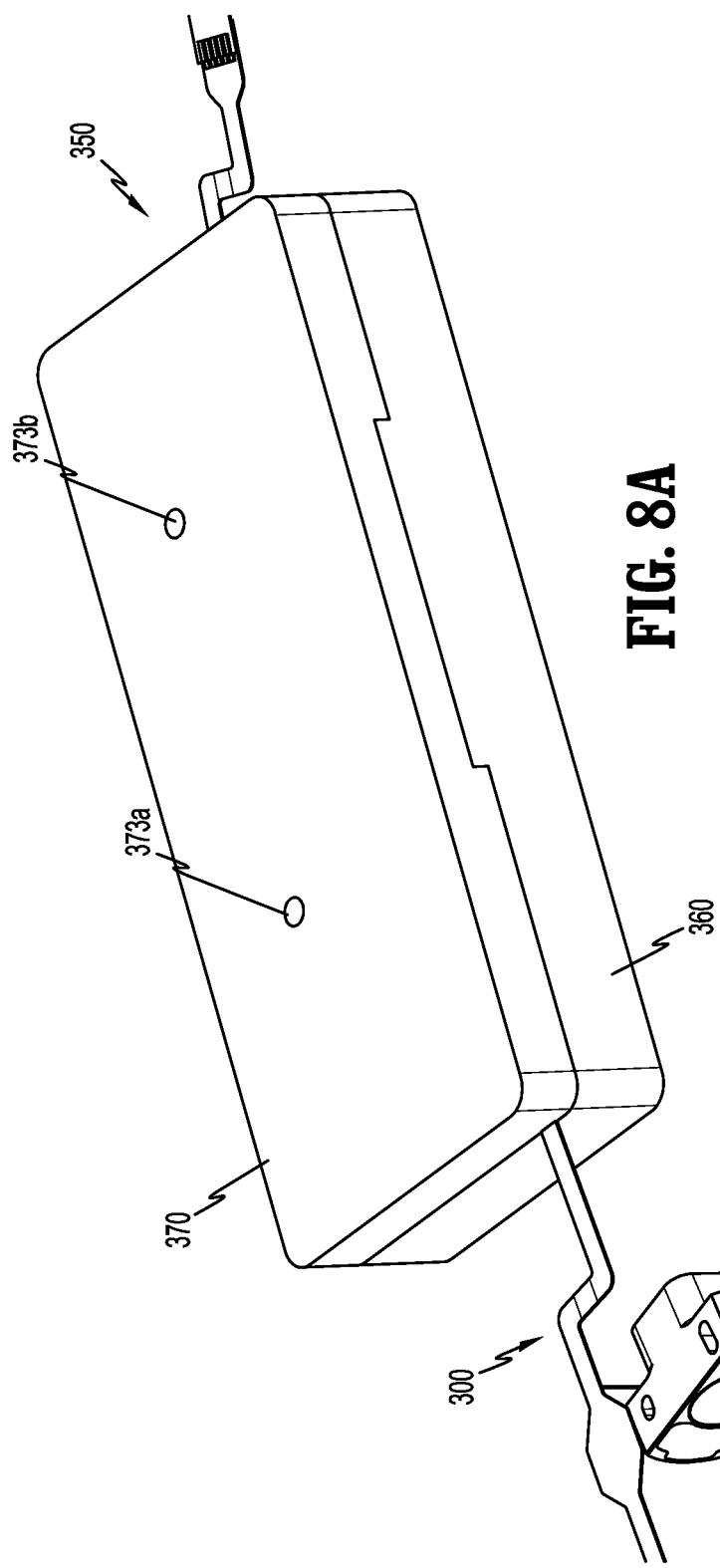
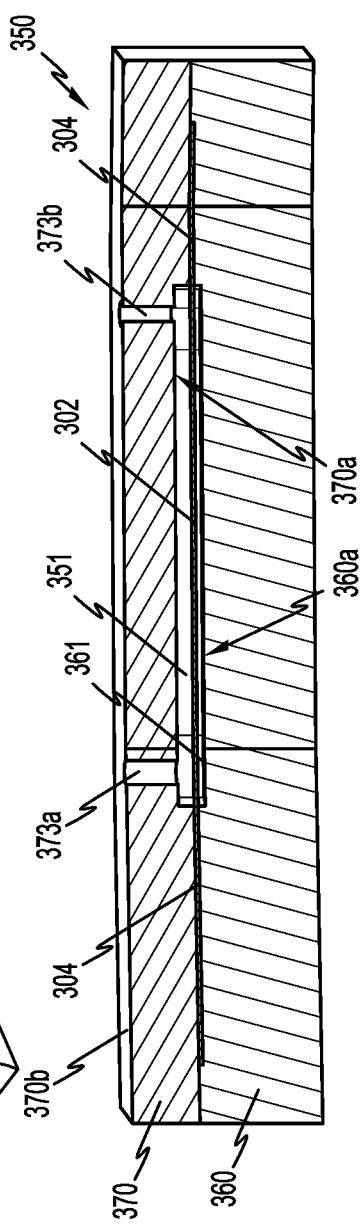

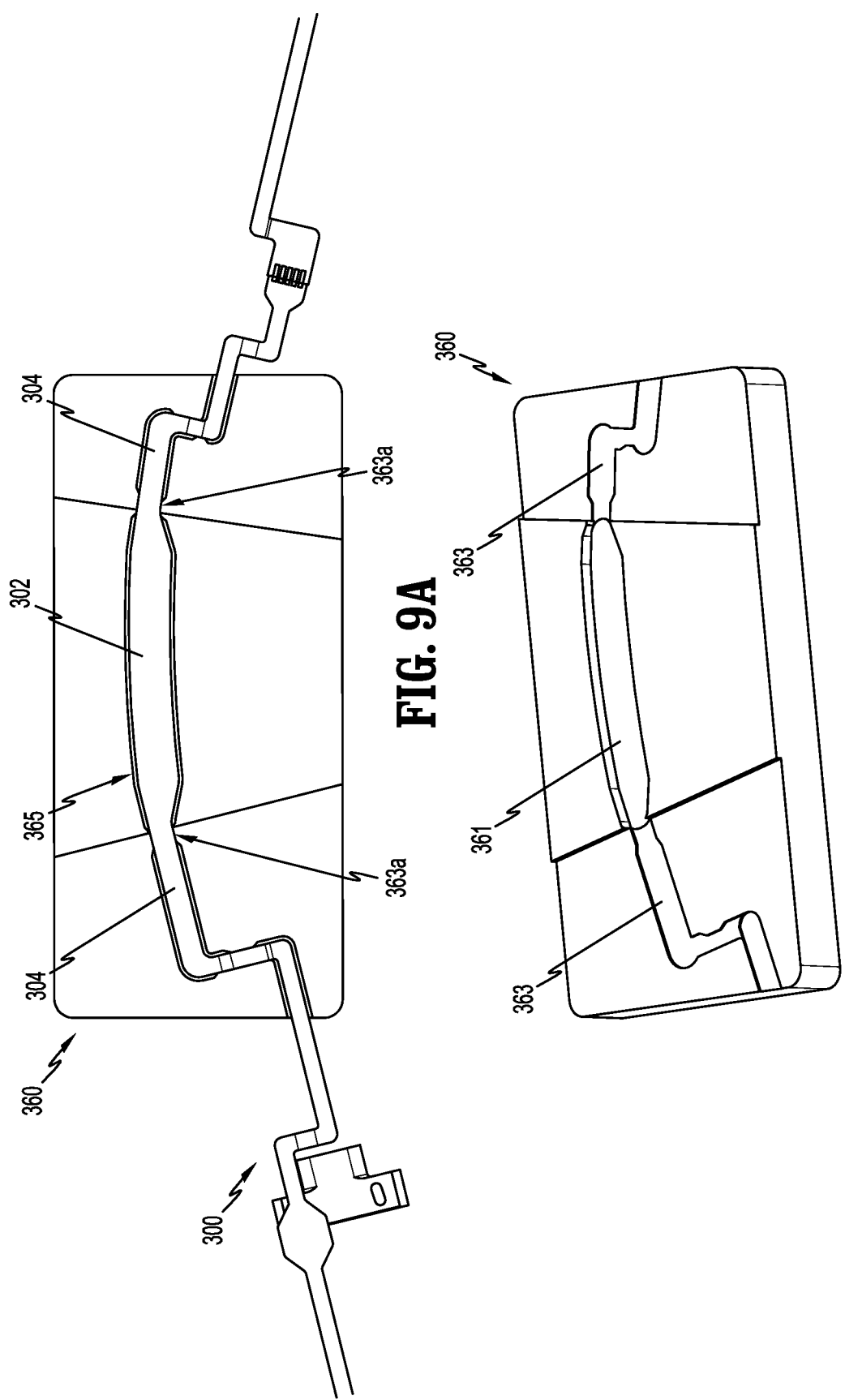

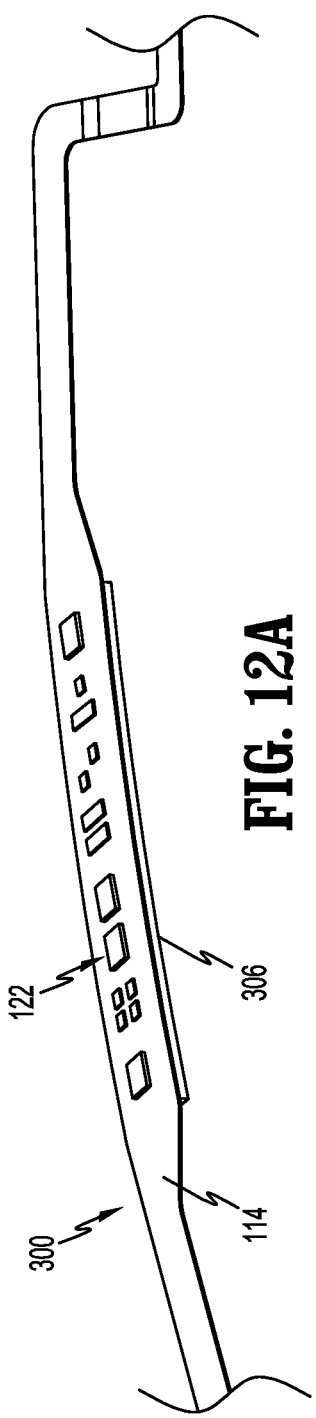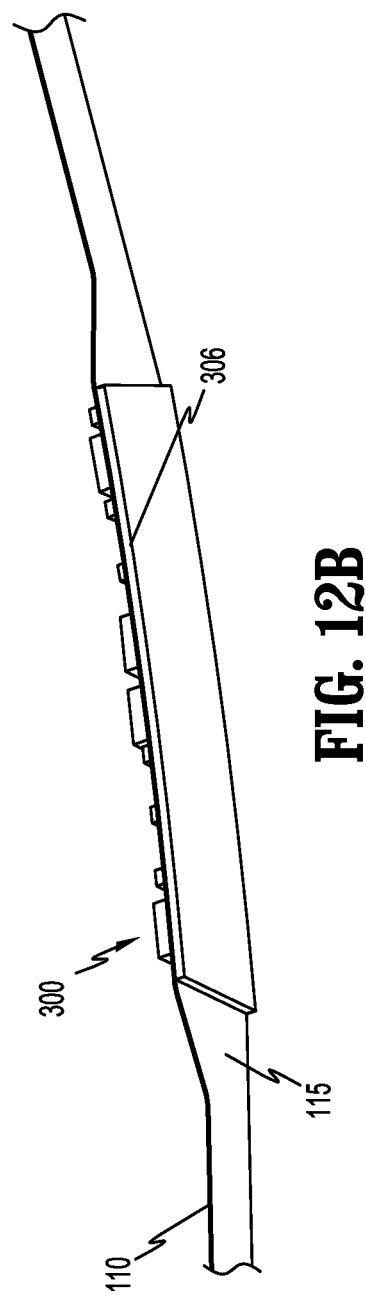

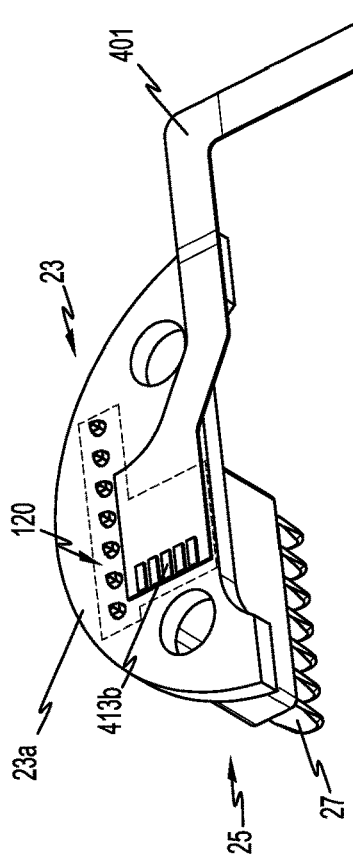
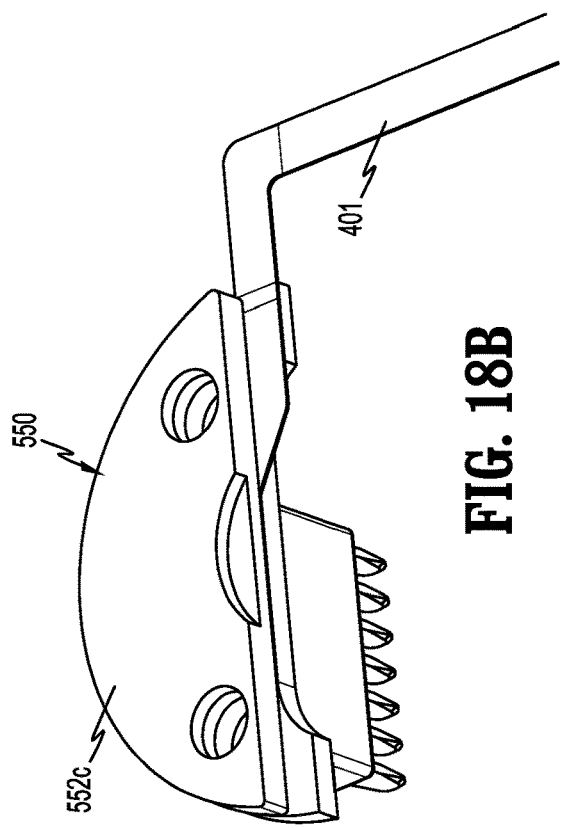
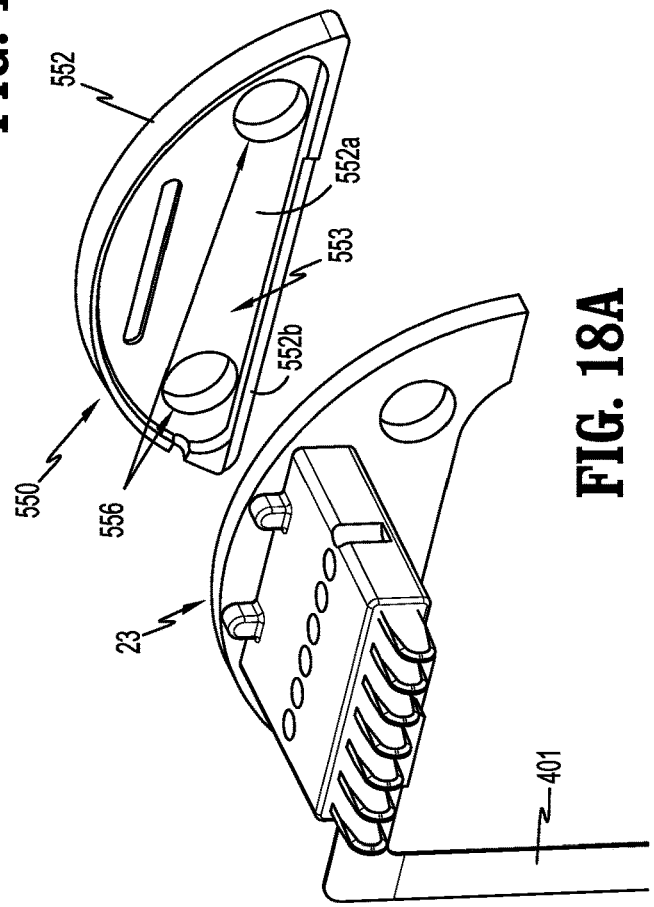

FULLY ENCAPSULATED ELECTRONICS AND PRINTED CIRCUIT BOARDS

CROSS-REFERENCE TO RELATED APPLICATIONS

This application is a Continuation-in-Part application claiming the benefit of and priority to U.S. patent application Ser. No. 15/947,314, filed Apr. 6, 2018, which claims the benefit of, and priority to, U.S. Provisional Patent Application No. 62/508,101, filed May 18, 2017, the entire content of each of which is hereby incorporated herein by reference.

TECHNICAL FIELD

The present disclosure relates generally to reusable surgical devices. More particularly, the present disclosure relates to powered surgical devices with enhanced durability and increased moisture resistance.

BACKGROUND

Powered surgical devices include electronic components, such as printed circuit boards, switches, sensors, etc., to enhance the control of functions of the surgical devices. The intelligence of such surgical devices result in a higher product cost compared to currently available disposable units. Accordingly, it would be beneficial if such intelligent devices are reusable.

For example, surgical devices in the form of surgical stapling apparatus are employed by surgeons to sequentially or simultaneously apply one or more rows of fasteners, e.g., staples or two-part fasteners, to body tissue for the purpose of joining segments of body tissue together and/or attaching a surgical implant to body tissue. Disposable surgical stapling apparatus are used to perform various stapling functions in surgery, such as performing anastomosis of tubular body structures (e.g., the colon, the stomach, the small intestine, etc.) in an end to end, end to side, or side to side manner. Once the procedure is complete, the device is discarded. Reusable surgical stapling apparatus are also used to perform various stapling functions in surgery, and the use thereof may result in lower cost of a procedure over the life of the device.

Powered surgical stapling apparatus include electronic components to monitor and facilitate functions, such as clamping, stapling, and/or cutting forces of the device. For example, load reading sensors can be used to detect pre-set loads and cause the device to react to such a response. For instance, during clamping of thick tissue, the load will rise to a pre-determined limit where the device can slow clamping to maintain the clamping force as the tissue relaxes. This allows for clamping of thick tissue without damage to such tissue (e.g., serosa tears).

Reusable surgical devices must be cleaned and sterilized prior to subsequent uses. Cleaning and sterilization procedures, however, are aggressive in nature. Cleaning (e.g., washing and/or disinfecting) utilizes alkaline solutions having high pH values (e.g., a pH of 11). Autoclaving (a common method of sterilization) utilizes high pressure superheated steam (e.g., 30 PSI@160° C. for 20 minutes). Such environments are known to damage various electronic components. For example, surgical devices may suffer from moisture ingress during cleaning and/or sterilizing procedures which, in turn, may corrode and/or degrade the electronic components.

The electronic components of reusable surgical devices may be protected from high temperatures, steam, and/or moisture by utilizing, for example, conformal coatings, potting, sealed enclosures, and/or overmolding. The electronic components, however, may still suffer from moisture ingress during cleaning and/or sterilizing procedures (e.g., cracking or delamination of conformal coatings), and/or may be damaged during application of the protective materials (e.g., heat damage during sealing of enclosures).

Thus, it would be beneficial if the durability of the electronic components is enhanced to improve the reliability of the electronic components and/or extend the effective cycle life of the surgical devices.

SUMMARY

The surgical devices of the present disclosure include a printed circuit board having electronic components housed within a hermetically sealed and/or encapsulated chamber. The electronic components are thus protected and configured to withstand environmental stresses associated with high pH cleaning and sterilization (e.g., autowashing and/or autoclaving), thereby rendering the electronic components more durable for re-use. Additionally, methods of the present disclosure include integrating and hermetically sealing and/or encapsulating the electronic components of the printed circuit board to minimize and/or prevent damage which may occur to the electronic components during the assembly process.

In one aspect of the present disclosure, a method of assembling a hermetically sealed printed circuit board includes: securing a first end portion of a wall of a cap to a substrate around an electrical contact region of the substrate, the wall including a second end portion disposed in an open configuration; mounting an electronic component to the electrical contact region of the substrate; and sealing the second end portion of the wall closed to form a hermetically sealed chamber between the substrate and the cap to encase the electronic component therein.

In embodiments, securing the wall of the cap includes bonding the first end portion of the wall to the substrate. In some embodiments, the first end portion of the wall includes a flange and bonding the first end portion includes welding the flange to the substrate.

The substrate may be a flex cable, and mounting the electronic component may include forming a printed circuit board on the flex cable.

In embodiments, sealing the second end portion of the wall includes heat sealing sections of the wall together. In some embodiments, sealing the second end portion of the wall includes securing a cover of a cap to the wall.

Mounting the electronic component may include positioning the electronic component of the substrate a spaced distance from outer edges of the substrate, and securing the first end portion of the wall of the cap to the substrate may include bonding the first end portion to the outer edges of the substrate. Mounting of the electronic component may be performed prior or subsequent to securing the first end portion of the wall of the cap to the substrate.

In embodiments, the method further includes placing the substrate in an inert gas environment prior to mounting the electronic component and sealing the second end portion of the wall. In some embodiments, the method further includes applying a coating over the electronic component prior to sealing the second end portion of the wall.

In another aspect of the present disclosure, a method of assembling a flex cable and integrating the flex cable into a surgical device includes: assembling electronic components on a first side of a substrate of a flex cable within a perimeter of a wall secured to the substrate, the wall extending transversely from the first side of the substrate and terminating at an open end; and closing the open end of the wall such that the electronic components are disposed within a sealed chamber.

Assembling the electronic components may include forming a printed circuit board on the flex cable. The method may include placing the flex cable in an inert gas environment prior to assembling the electronic components and closing the open end of the wall, and/or applying a conformal coating over the electronic components prior to closing the open end of the wall.

The method may include placing the flex cable into an adapter assembly of the surgical device. In embodiments, the method further includes electrically connecting the flex cable to a sensor disposed within the adapter assembly. In some embodiments, the method further includes electrically connecting the flex cable with a handle assembly and an end effector of the surgical device to enable communication between the handle assembly, the adapter assembly, and the end effector.

According to a further aspect of the present disclosure, a hermetic electronic assembly includes a printed circuit board and a cap. The printed circuit board includes a plurality of electronic components disposed on a first side thereof and offset a distance from outer edges of the printed circuit board. The cap includes a wall having a first end portion and a second end portion. The first end portion is bonded to the printed circuit board entirely around the plurality of electronic components and the second end portion is heat sealed closed a distance spaced from the plurality of electronic components. The bonding of the first end portion to the printed circuit board and the heat sealing of the second portion of the wall together form a hermetic seal encasing the plurality of electronic components therein.

In embodiments, the first end portion of the cap includes a flange, and the flange is bonded to the outer edges of the printed circuit board. The printed circuit board may be a flex cable.

In another aspect of the present disclosure, a method of encapsulating and hermetically sealing a printed circuit board of a flex cable includes: positioning a printed circuit board portion of a flex cable into a channel defined in a first mold half of a mold, the printed circuit board portion including a substrate and electronic components mounted on the substrate; mounting a second mold half onto the first mold half to enclose the channel of the first mold half and form a cavity within the mold; and filling the cavity of the mold with an encapsulation material through an inlet opening defined through the mold.

The method may include positioning arm portions of the flex cable in grooves defined in the first mold half, the grooves extending from opposed sides of the channel. In embodiments, mounting the second mold half onto the first mold half further includes retaining the arm portions under tension between the first and second mold halves such that the printed circuit board portion of the flex cable is disposed in spaced relation relative to inner surfaces of the first and second mold halves defining the cavity of the mold. In embodiments, filling the cavity of the mold further includes completely covering the printed circuit board portion of the flex cable with the encapsulation material.

In embodiments, filling the cavity of the mold further includes filling the cavity until the encapsulation material vents through an outlet opening defined through the mold.

The method may further include opening the mold after the encapsulation material has solidified within the cavity and removing the flex cable from the mold. In some embodiments, the method further includes curing the encapsulation material within the cavity of the mold under vacuum.

In some embodiments, the method further includes clamping outer edges of the encapsulation material to enhance the bond between the encapsulation material and the flex cable. In certain embodiments, the method includes attaching a rigidizing layer to the substrate of the printed circuit board portion of the flex cable prior to positioning the printed circuit board portion into the channel of the first mold half.

According to yet another aspect of the present disclosure, a method of encapsulating and hermetically sealing electronic components of a flex cable assembly and integrating the flex cable assembly into a surgical device includes: positioning a printed circuit board portion of a flex cable assembly into a channel defined in a first housing half of an encapsulation housing, the printed circuit board portion including a substrate of a first flex cable of the flex cable assembly and electronic components mounted on the substrate; mounting a second housing half onto the first housing half to enclose the channel of the first housing half and form a cavity within the encapsulation housing; and filling the cavity of the encapsulation housing with an encapsulation material through an inlet opening defined through the encapsulation housing.

The method may include positioning arm portions of the flex cable through cut-outs defined in side surfaces of the first housing half of the encapsulation housing.

In embodiments, the printed circuit board portion of the flex cable assembly is disposed in spaced relation relative to the inner surfaces of the first and second housing halves defining the cavity of the encapsulation housing and filling the cavity of the encapsulation housing further includes completely covering the printed circuit board portion of the flex cable assembly with the encapsulation material. In some embodiments, the inner surface of the first housing half includes standoffs disposed thereon to maintain space between the printed circuit board portion of the flex cable assembly and the inner surface of the first housing half, and positioning the printed circuit board portion into the channel further includes positioning the printed circuit board portion on top of the standoffs.

Filling the cavity of the encapsulation housing may further include filling the cavity until the encapsulation material vents through an outlet opening defined through the encapsulation housing. In some embodiments, the method further includes orienting the encapsulation housing so that the inlet opening is lower than the outlet opening prior to filling the cavity with the encapsulation material.

The method may further include curing the encapsulation material within the encapsulation housing and attaching the encapsulation housing to a component disposed within a surgical device. In embodiments, attaching the encapsulation housing to the component further includes placing the flex cable assembly and the encapsulation housing into an adapter assembly of the surgical device.

In embodiments, the method further includes connecting an electrical contact region of a second flex cable of the flex cable assembly to a rigid printed circuit board; positioning a second encapsulation housing over the rigid printed circuit board such that electronic components of the rigid printed circuit board and the electrical contact region of the second flex cable are disposed within a cavity defined between the encapsulation housing and the rigid printed circuit board;

and filling the cavity with an encapsulation material through an inlet opening defined through the second encapsulation housing.

In some embodiments, the method further includes curing the encapsulation material within the second encapsulation housing and attaching the second encapsulation housing to a component disposed within a surgical device.

Other aspects, features, and advantages will be apparent from the description, drawings, and the claims.

BRIEF DESCRIPTION OF THE DRAWINGS

Various aspects of the present disclosure are described herein below with reference to the drawings, which are incorporated in and constitute a part of this specification, wherein:

FIG. 3A is a perspective view of a flex cable of the wiring harness of FIG. 2, illustrating assembly of a cap, in an open configuration, on a substrate of the flex cable in accordance with an embodiment of the present disclosure;

FIG. 3B is a cross-sectional view of the flex cable of FIG. 3A, taken along line 3B-3B of FIG. 3A;

FIG. 4 is a top view of the flex cable of FIGS. 3A and 3B, illustrating assembly of electronic components on the substrate of the flex cable;

FIG. 5A is a perspective view of the flex cable of FIGS. 3A-4, illustrating closing of the cap towards a closed configuration;

FIG. 5B is a cross-sectional view of the flex cable of FIGS. 3A-5A, illustrating sealing of the cap to the closed configuration;

FIG. 6 is a perspective view of a flex cable in accordance with another embodiment of the present disclosure;

FIG. 8A is a perspective view of the mold of FIG. 7, in a closed or assembled state;

FIG. 8B is a cross-sectional view of the mold of FIG. 8A;

FIG. 9A is a top view of a first mold half of the mold of FIG. 7, including the flex cable positioned therein;

FIG. 9B is a top, perspective view of the first mold half of FIG. 9A;

FIG. 12A is a top, perspective view of the flex cable of FIG. 7 in accordance with another embodiment of the present disclosure;

FIG. 12B is a side view of the flex cable of FIG. 12A;

FIG. 17 is a perspective view of a second flex cable of the wiring harness of FIG. 13 coupled to an electrical assembly of the adapter assembly of FIG. 1 in accordance with an embodiment of the present disclosure;

FIG. 18A is a perspective view of the second flex cable and the electrical assembly of FIG. 17, and an encapsulation housing in accordance with an embodiment of the present disclosure;

FIGS. 18B and 18C are a perspective view of the encapsulation housing secured to the electrical assembly of FIG. 18A.

DETAILED DESCRIPTION

Figure 1:
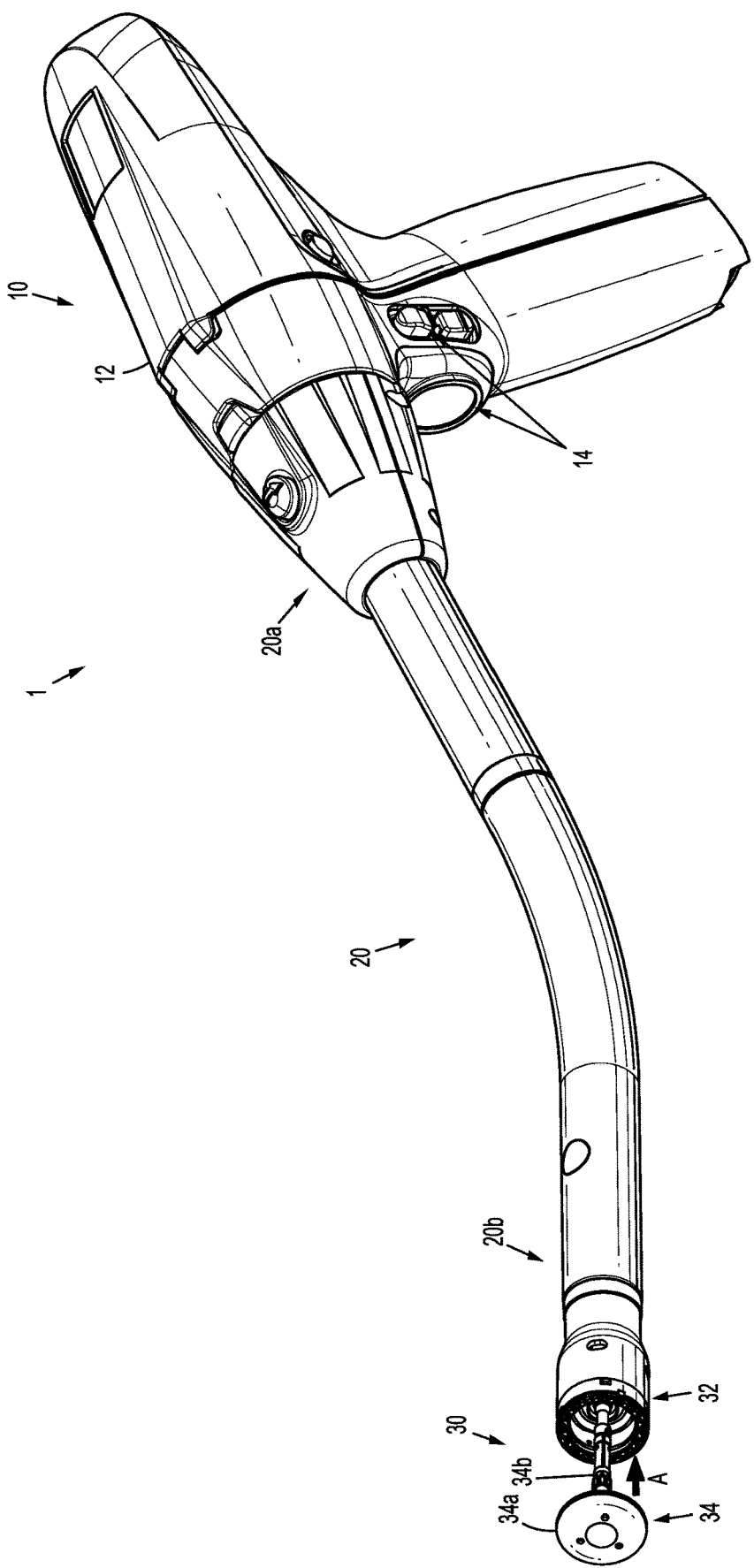
FIG. 1 is a perspective view of a surgical device in accordance with an embodiment of the present disclosure.

Surgical devices in accordance with embodiments of the present disclosure include a printed circuit board having electronic components disposed within a hermetically sealed or encapsulated chamber to protect the electronic components from exposure to moisture during, for example, cleaning and/or sterilizing procedures where the surgical devices may be subjected to high temperatures, steam, chemicals, and/or moisture. The electronic components of the surgical devices of the present disclosure are protected to prevent and/or resist breakdown over multiple/repeated cleaning and sterilizing cycles.

While the present disclosure is directed to printed circuit boards integrated on a flexible or flex cable of a surgical device, it is envisioned that the principles of the present disclosure are equally applicable to a range of printed circuit boards (e.g., rigid printed circuit boards, such as FR4 circuit boards) and electronic components (e.g., sensors) housed within reusable surgical devices.

Embodiments of the present disclosure are now described in detail with reference to the drawings in which like reference numerals designate identical or corresponding elements in each of the several views. Throughout this description, the term "proximal" refers to a portion of a device, or component thereof, that is closer to a user, and the term "distal" refers to a portion of the device, or component thereof, that is farther from the user.

Turning now to FIG. 1, a surgical device 1 in accordance with an embodiment of the present disclosure is shown. The surgical device 1 is in the form of a powered handheld electromechanical surgical instrument, and includes a powered handle assembly 10, an adapter assembly 20, and a tool assembly or end effector 30. The powered handle assembly 10 is configured for selective connection with the adapter assembly 20 and, in turn, the adapter assembly 20 is configured for selective connection with the end effector 30.

The surgical device 1 will only further be described to the extent necessary to disclose aspects of the present disclosure. For a detailed description of the structure and function of exemplary surgical devices, reference may be made to commonly owned U.S. Patent Publication Nos. 2016/0296234, ("the '234 Publication"), and 2016/0310134 ("the '134 Publication"), the entire content of each of which is incorporated herein by reference.

With continued reference to FIG. 1, the handle assembly 10 includes a handle housing 12 housing a power-pack (not shown) configured to power and control various operations of the surgical device 1, and a plurality of actuators 14 (e.g., finger-actuated control buttons, knobs, toggles, slides, interfaces, and the like) for activating various functions of the surgical device 1. The adapter assembly 20 includes a proximal portion 20a configured for operable connection to the handle assembly 10 and a distal portion 20b configured for operable connection to the end effector 30. The end effector 30 including a loading unit 32 having a plurality of staples (not shown) disposed therein and an anvil assembly 34 including an anvil head 34a and an anvil rod 34b.

For a detailed description of exemplary handle assemblies, adapter assemblies, and end effectors which may be utilized in a surgical device of the present disclosure, reference may be made to the '234 and '134 Publications, the entire content of each of which was previously incorporated herein by reference.

Figure 2:
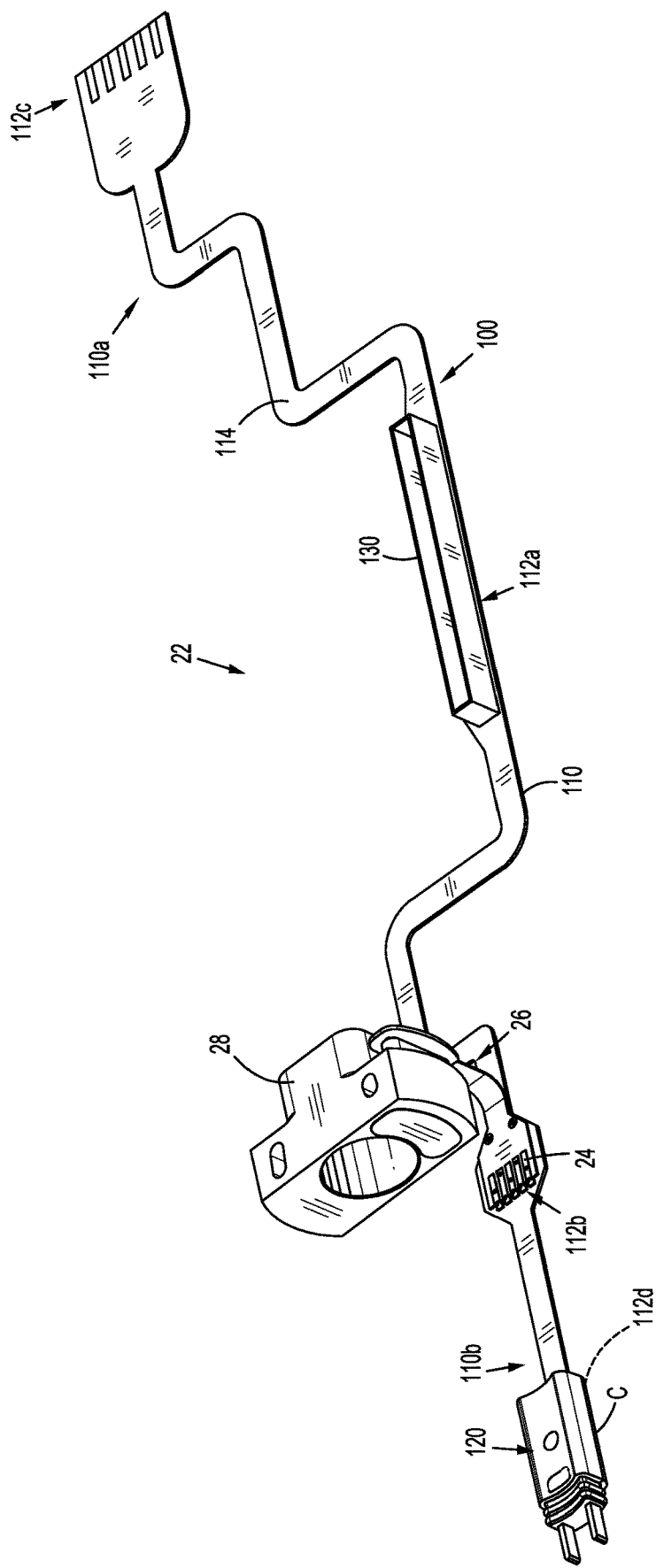
FIG. 2 is a perspective view of a wiring harness of an adapter assembly of the surgical device of FIG. 1.

With reference now to FIG. 2, in conjunction with FIG. 1, the adapter assembly 20 includes a wiring harness 22 having at least one flex cable 100 electronically interconnecting the handle assembly 10 and the end effector 30 of the surgical device 1. The wiring harness 22 of the adapter assembly 20 is configured to enable communication between the handle assembly 10 and the end effector 30, and to relay power from the handle assembly 10 to the end effector 30. For example, this communication allows for calibration and communication of data and control signals between the end effector 30 and the adapter assembly 20, as well as between the adapter assembly 20 and the handle assembly 10, thereby transferring data pertaining to the end effector 30 to the handle assembly 10 and signals from the handle assembly 10 to the end effector 30.

The flex cable 100 includes a body or substrate 110 suitable for supporting and/or electrically connecting electronic components 120 thereto. The substrate 110 is formed from one or more layers or sheets of dielectric material, such as a polymer or a ceramic, and one or more layers of conductive material, such as copper foil, that form conductive traces (not explicitly shown) in the substrate 110. Vias (not shown) may interconnect the conductive traces through different layers of the flex cable 100.

In embodiments, the substrate 110 of the flex cable 100 is formed from copper-clade polyimides, such as PYRALUX® or NIKAFLEX®, which are registered trademarks owned by DuPont. In some embodiments, the substrate 110 is formed from high temperature materials, such as PYRALUX® HT, also a registered trademark owned by DuPont. It should be understood that the substrate 110 is configured to allow for the fabrication of single or double sided flex circuits, multilayer flex circuits, and rigid flex circuits. The layers of the substrate 110 may be joined to one another by, for example, laminating, welding, and/or using adhesives, among other methods and materials within the purview of those skilled in the art.

A plurality of electrical contact regions 112 (referred to herein as first, second, third, and fourth electrical contact regions 112a-d) are disposed at terminal ends of the conductive traces (not shown) defined through the substrate 110 on a first side 114 of the flex cable 100. Each of the plurality of electrical contact regions 112 includes one or more pads (e.g., solder pads) to which electronic components 120 are joined (e.g., soldered). The electronic components 120 may be, for example, surface mount technology and/or through-hole technology, including, for example, integrated circuits (e.g., microchips, microcontrollers, microprocessors), resistors, amplifiers, inductors, capacitors, sensing elements (e.g., optical sensors, pressure sensors, capacitive sensors), buttons, switches, circuit boards, electrical connectors, cables, and/or wires, among other elements or circuitry within the purview of those skilled in the art.

The first electrical contact regions 112a includes electronic components 120 (see e.g., FIG. 4) disposed thereon. A cap 130 is disposed over the first electrical contact region 112a to hermetically seal the electronic components 120 therein, as described in further detail below. The second electrical contact region 112b is in the form of solder pads which are aligned and soldered to solder pads 24 of an adapter flex cable 26 which, in turn, is electrically coupled to a force sensor 28 disposed within the adapter assembly 20 (FIG. 1) for measuring forces of the end effector 30 (e.g., as shown in FIG. 1, the pressure applied by the anvil head 34a in the direction of arrow "A" against the distal portion 20b of the adapter assembly 20, the pressure applied by tissue acting on the anvil head 34a in a direction opposite of arrow "A" as the anvil head 34a is closed onto tissue, etc.).

With continued reference to FIG. 2, a proximal portion 110a of the substrate 110 includes the third electrical contact region 112c configured for electrical connection with the handle assembly 10 (FIG. 1). A distal portion 110b of the substrate 110 includes the fourth electrical contact region 112d (shown in phantom) coupled to an electronic component 120 in the form of an electrical connector "C" for electrical connection with the end effector 30 (FIG. 1).

It should be understood that while the flex cable 100 is shown including four electrical contact regions 112, the flex cable 100 may have any number of electrical contact regions depending upon the desired configuration and functionality of the flex cable 100, as is within the purview of those skilled in the art.

Referring now to FIGS. 3A-5B, a method of integrating and hermetically sealing a printed circuit board 122 to the substrate 110 of the flex cable 100 in accordance with an embodiment of the present disclosure is shown. As shown initially in FIGS. 3A and 3B, a cap 130, in an initial open-ended configuration, is joined to the substrate 110 of the flex cable 100 such that a wall 132 of the cap 130 extends transversely from the first side 114 of the substrate 110 and defines a closed perimeter around the first electrical contact region 112a of the substrate 110. The wall 132 may be sized to be complementary in shape with the first electrical contact region 112a of the substrate 110. The wall 132 may be formed from the same material or a different material from that of the substrate 110 (e.g., the same or a different polymeric material).

A first end portion 132a of the wall 132 includes a flange 134 that provides a flat surface or increased surface area for bonding of the wall 132 to the substrate 110. The first end portion 132a of the wall 132 may be secured to the substrate 110 by, for example, laminating or welding the flange 134 around an entire perimeter thereof to the substrate 110 to seal and form a leak-proof barrier at the junction of the substrate 110 and the cap 130. The flange 134 is positioned adjacent to and is aligned with outer edges 116 of the substrate 110, and extends along the outer edges 116 as well as across the substrate 110. A second end portion 132b of the wall 132 is open to provide access to the first electrical contact region 112a of the substrate 110. Accordingly, the cap 130 is open-ended during the initial stages of assembling the flex cable 100.

As shown in FIG. 4, electronic components 120 are assembled onto the substrate 110 at the first electrical contract region 112a disposed within the wall 132 of the cap 130 to form a printed circuit board 122. The electronic components 120 are disposed on the substrate 110 in spaced relation relative to the wall 132 of the cap 130 such that the electronic components 120 are offset a distance from the outer edge 116 of the substrate 110 to which the flange 134 of the cap 130 is bonded, as well as the portions of the flange 134 extending across the substrate 110. Placement of the electronic components 120 onto the substrate 110 in spaced relation relative to the flange 134 of the cap 130 and/or placement of the electronic components 120 onto the substrate 110 after securing the wall 132 to the substrate 110 prevents damage to the electronic components 120 that may have occurred due to heat transfer during bonding of the flange 134 to the substrate 110.

Bonding processes may require high temperatures and/or high pressure which may transfer to the substrate 110. For example, in embodiments in which the substrate 110 and the wall 132 are formed from high temperature materials, high temperatures and/or long bonding times may be required to secure the wall 132 to the substrate 110. Accordingly, assembling the electronic components 120 onto the substrate 110 a spaced distance from the flange 134 of the cap 130 either prior to or after securing the wall 132 to the substrate 110 minimizes potential damage to the electronic components 120. Further, assembling the electronic components 120 onto the substrate 110 after securing the wall 132 to the substrate 110 mitigates potential damage to the electronic components 120.

As shown in FIGS. 5A and 5B, after the electronic components 120 are assembled onto the substrate 110 of the flex cable 100, the cap 130 is sealed to a closed configuration by joining together the second end portion 132b of the wall 132. The second end portion 132b of the wall 132 is gathered and secured together in a fluid tight manner to define a hermetically sealed chamber 135 housing the electronic components 120 therein. As specifically shown in FIG. 5A, for example, the second end portion 132b of first and second sections 133a, 133b of the wall 132 are moved from an open position (see e.g., first section 133a) to a closed position (see e.g., second section 133b) so that, as shown in FIG. 5B, the second end portion 132b of the first and second sections 133a, 133b can be secured together along the entire length of the junction thereof. The second end portion 132b of the wall 132 may be secured together by, for example, laminating or welding the second end portion 132b of the wall 132 together to seal and form a leak-proof barrier at the second end portion 132 of the wall 132. Accordingly, the cap 130 is close-ended at the end stages of assembling the flex cable 100.

The space provided by the wall 132 around the electronic components 120 minimizes damage which may occur during the process of closing the second end portion 132b of the wall 132 (e.g., by spacing the second end portion 132 of the wall 132 a distance from the electronic components 120 so that heat from the bonding process does not reach the electronic components 120). The height of the wall 132 may vary depending, for example, on the space and/or distance needed to optimize protection of the electronic components 120 from the settings (e.g., heat) of the bonding process utilized. The second end portion 132b of the wall 132 may be shaped (e.g., have a domed shape) to provide additional space within the cap 130 for the electronic components 120.

While the wall 132 is shown as a single piece that is secured to the substrate 110 and to itself at the second end portion 132b thereof to form the hermetically sealed chamber 135, other configurations of the cap 130 are envisioned. For example, as shown in FIG. 6, a flex cable 200 includes a substrate 110, electronic components 120 (see e.g., FIG. 4) assembled onto the substrate 110, and a cap 230 including a wall 232 secured to the substrate 110 at a first end portion 232a thereof around the electronic components 120, and a cover 236 positioned over and secured to a second end portion 232b of the wall 232 in a fluid tight manner to define a hermetically sealed chamber 235 (shown in phantom) housing the electronic components 120 (see e.g., FIG. 4) therein. The cover 236 may be secured to the wall 232 by, for example, laminating or welding the entire outer perimeter of the cover 236 to the second end portion 232b of the wall 232 to seal and form a leak-proof barrier between the wall 232 and the cover 236. The cover 236 may be formed from the same material or a different material from that of the wall 232.

Assembly of the flex cable 100, 200 may be performed using vacuum or in the presence of an inert gas (e.g., argon, nitrogen, etc.), as is within the purview of those skilled in the art. In embodiments, the electronic components 120 are assembled onto the substrate 110 and sealed with the cap 130, 230 by fully drying, assembling, and sealing the electronic components 120 in an inert gas environment, such as an inert glove box (e.g., a nitrogen-filled atmosphere), to ensure zero moisture content within the electronic components 120 and the hermetically sealed chamber 135, 235.

In embodiments, a coating may be disposed over the electronic components 120 prior to sealing with the cap 130, 230. The coating may be a conformal coating that protects the electronic components 120 against moisture and/or heat. Accordingly, the coating may act as an additional layer of protection from any heat that may be produced while sealing the cap 130, 230 and/or in the event that the seal should fail and moisture should permeate or ingress through the cap 130, 230, the coating may provide a layer of protection from the moisture that may otherwise attack the substrate 110 and/or electronic components 120.

In an embodiment, it is further contemplated that a moisture collection agent, e.g., a desiccant, may be provided within the void of the cap 130, 230, prior to the sealing of the cap 130, 230 to the closed configuration. For a detailed description of moisture collection agents, for use in flex circuits and the like, reference may be made to U.S. Provisional Patent Application Ser. No. 62/464,584, filed on Feb. 28, 2017, now U.S. patent application Ser. No. 15/876,378, filed on Jan. 22, 2018, the entire content of each of which is incorporated herein by reference.

Figure 7:
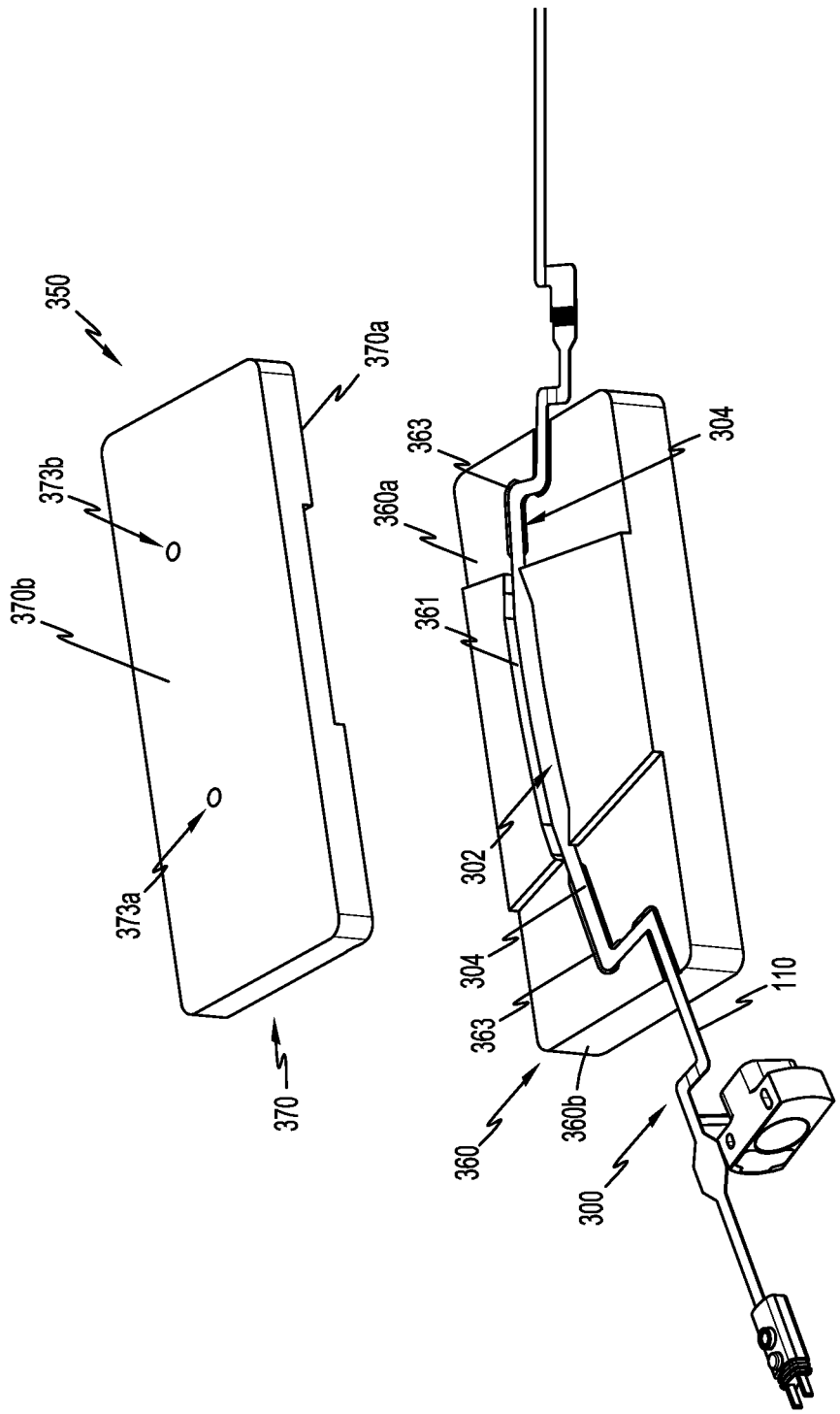
FIG. 7 is a perspective view of a mold, in an open or separated state, for encapsulating a portion of a flex cable in accordance with an embodiment of the present disclosure.

Turning now to FIG. 7, a mold 350 for encapsulating and hermetically sealing the printed circuit board 122 (FIG. 12A) of a flex cable 300 in accordance with an embodiment of the present disclosure is shown. The flex cable 300 is substantially identical to the flex cable 100 of FIG. 2-6 except the flex cable 300 does not include a cap 130, 230 and the printed circuit board 122 is assembled onto the substrate 110 prior to positioning the flex cable 300 in the mold 350.

The mold 350 includes first and second mold halves or portions 360, 370. The first mold half 360 includes a first or inner surface 360a having a channel 361 defined therein, as well as grooves 363 extending from opposed sides of the channel 361 to side surfaces 360b of the first mold half 360. The channel 361 is sized and shaped to receive a printed circuit board portion 302 of the flex cable 300 therein (e.g., the portion of the substrate 110 including the printed circuit board 122), and the grooves 363 are sized and shaped to receive arm portions 304 of the flex cable 300 therein (e.g., the portions of the substrate 110 extending away from the printed circuit board portion 302). The first surface 360a of the first mold half 360 may be a stepped surface wherein a central portion of the first surface 360a containing the channel 361 is raised relative to outer portions of the first surface 360a containing the grooves 363.

As shown in FIGS. 7-8B, the second mold half 370 includes a first or inner surface 370a having a complementary geometry to the first surface 360a of the first mold half 360 so that when the first surfaces 360a, 370a of the first and second mold halves 360, 370 mate, the first surface 370a of the second mold half 370 extends over the channel 361 defined in the first mold half 360 to form a cavity 351 within the mold 350. Additionally or alternatively, the first surface 370a of the second mold half 370 may include a channel (not shown) defined therein that corresponds with the channel 361 of the first mold half 360 so that collectively, the channels form the cavity of the mold.

The second mold half 370 further includes an inlet opening or sprue 373a and an outlet opening or vent 373b extending through a second or outer surface 370b of the second mold half 370 and through the first surface 370a into the cavity 351 of the mold 350. The inlet opening 373a allows for passage of an encapsulation material 352 (FIG. 10A) into the cavity 351 of the mold 350, and the outlet opening 373b allows for the encapsulation material to vent when the cavity 351 of the mold 350 is fully filled with the encapsulation material. The cavity 351 of the mold 350 is sized and shaped to retain the printed circuit board portion 302 of the flex cable 300 in spaced relation relative to the portions of the first surfaces 360a, 370a of the first and second mold halves 360, 370 defining the cavity 351 and to receive the encapsulation material around the printed circuit board portion 302 of the flex cable 300 such that the printed circuit board portion 302 is fully covered by the encapsulation material.

It should be understood that while the inlet and outlet openings 373a, 373b are shown disposed in fluid communication with the second mold half 370, the inlet and outlet openings 373a, 373b may be located in, and extend through any portion of the mold 350 so long as the inlet opening 373a is positioned to permit fluid communication between the cavity 351 of the mold 350 and a source of the encapsulation material, and the outlet opening 373b is positioned to permit fluid communication between the cavity 351 and the outside environment.

The encapsulation material may be, for example, urethanes, acrylics, epoxies, among other materials that are flexible in nature so that the encapsulation material can move with the thermal and mechanical movement of the flex cable 300 and withstanding cleaning and sterilization cycles. The encapsulation material may be materials utilized to form flexible conformal coatings such as those sold under the trademark HUMISEAL® of Columbia Chase Corporation, or potting compounds such as those sold under the trademark DOLPHON® of John C. Dolph Company (e.g., polyurethane casting compounds such as DOLPHON® CB-1109).

As shown in FIGS. 8A-9B, the channel 361 of the first mold half 360 has a geometry optimized to locate and fully receive the printed circuit board portion 302 of the flex cable 300 therein on a repeatable basis. The channel 361 has a depth greater than a thickness of the printed circuit board portion 302 and a width larger than a width of the printed circuit board portion 302 such that a gap or border 365 of space extends around the printed circuit board portion 302 of the flex cable 300 when the printed circuit board portion 302 is positioned within the channel 361. As discussed above, the second mold half 370 has a geometry that is complementary to the geometry of the first mold half 360 to enclose the channel 361.

The grooves 363 of the first mold half 360 have a geometry optimized to locate and fully receive the arm portions 304 of the flex cable 300 therein. As specifically shown in FIGS. 8B and 9A, inner sections 363a of the grooves 363 have a depth and a width corresponding to a thickness and a width, respectively, of the arm portions 304 to secure the arm portions 304 therein in a substantially fluid tight manner and seal or shut off lateral sides of the cavity 351 of the mold 350 when the first and second mold halves 360, 370 are assembled together with the flex cable 300 disposed therebetween.

In a method of encapsulating the printed circuit board 122 of the flex cable 300, the flex cable 300 is positioned in the first mold half 360 with the printed circuit board portion 302 positioned within the channel 361 of the first mold half 360 and the arm portions 304 positioned within the grooves 363 as shown, for example, in FIG. 7. The second mold half 370 is then placed over the first mold half 360 such that the first surfaces 360a, 370a of the first and second mold halves 360, 370 abut each other and the channel 361 of the first mold half 360 is closed by the second mold half 370 to form the cavity 351 of the mold 350 as shown, for example, in FIGS. 8A and 8B. As discussed above, the cavity 351 defines a gap 365 (FIG. 9A) of space around the printed circuit board portion 302 of the flex cable 300 and the arm portions 304 are held under tension in a fluid tight relationship between the first and second mold halves 360, 370. After the first and second mold halves 360, 370 are mated, the first and second mold halves 360, 370 may be releasably secured together using, for example, clamps, bands, tape, etc.

The encapsulation material is then injected into the cavity 351 of the mold 350 through the inlet opening 373a until the encapsulation material emerges through the outlet opening 373b indicating that the cavity 351 is filled. The outlet opening 373b may thus provide a visual signal to a technician that the cavity 351 of the mold 350 is full. The encapsulation material is rendered into a liquid state for injection or pouring into the cavity 351 of the mold 350 by any method suitable for the type of encapsulation material utilized, as is within the purview of those skilled in the art. For example, the encapsulation material may be mixed, blended, and/or heated to activate or make the encapsulation material flowable. In some embodiments, to minimize deflection of the printed circuit board portion 302 of the flex cable 300 within the cavity 351 of the mold 350 during filling, a low injection pressure is employed.

The encapsulation material remains in the cavity 351 of the mold 350 until it has solidified or cured. Thereafter, the mold 350 is opened after, for example, unclamping the first and second mold halves 360, 370, and the now encapsulated flex cable 300 is removed therefrom. In embodiments, a release agent is applied to the first surfaces 360a, 370a of the first and second mold halves 360, 370 prior to placing the flex cable 300 into the mold 350 to ease removal of the flex cable 300 therefrom after encapsulation. In some embodiments, the first and second mold halves 360, 370 or the first surfaces 360a, 370a thereof are formed from a lubricious material such as a synthetic polymer (e.g., polyoxymethylene, acetal homopolymer, polytetrafluoroethylene) sold under the trademark DELRIN® or TEFLON®, both of E.I. Du Pont De Nemours and Company, to reduce the need for a release agent.

Casting of the encapsulation material may be performed using vacuum or in the presence of an inert gas (e.g., argon, nitrogen, etc.), as is within the purview of those skilled in the art. In embodiments, prior to injecting or pouring the encapsulation material into the mold, a vacuum is applied to the encapsulation material. In some embodiments, the encapsulation material is mixed and/or heated, poured into the mold, and then placed into a vacuum chamber. By pulling vacuum when the encapsulation material is in the liquid state, any bubbles, voids, and fluid porosity can be evacuated to form a solid encapsulate. In certain embodiments, the encapsulation material, the mold, and the flex cable are placed in a vacuum or inert gas environment, and the encapsulation material is mixed, casted, and cured under vacuum.

Figure 10A:
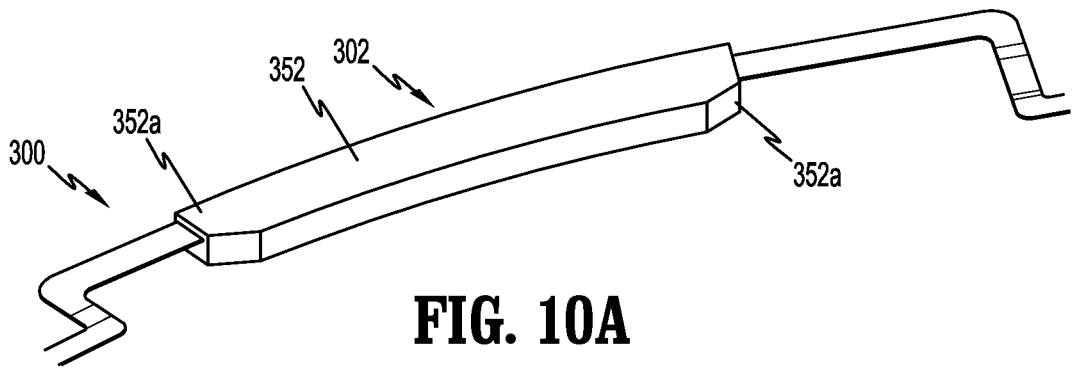
FIG. 10A is a side, perspective view of the flex cable after encapsulation within an encapsulation material via the mold of FIG. 7.
Figure 10B:
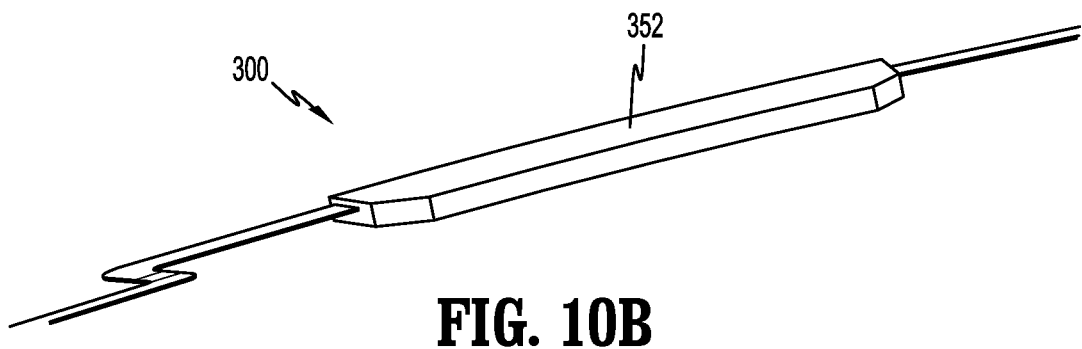
FIG. 10B is a side view of the flex cable of FIG. 10A.

As shown in FIGS. 10A and 10B, the flex cable 300 includes the encapsulation material 352 enveloped over the entirety of the printed circuit board portion 302 of the flex cable 300 after removal from the mold 350. The encapsulation material 352 covers the printed circuit board 122 (FIG. 12A) of the flex cable 300 and extends beyond the printed circuit board 122 such that the encapsulation material 352 maintains a substantially uniform thickness along the length thereof (e.g., the outer edges 352a of the encapsulation material 352 terminate at the same thickness as the portion of the encapsulation material 352 covering the printed circuit board 122). This configuration removes the feathered edge associated with traditional coating processes thereby enhancing the bond between the encapsulation material 352 and the flex cable 300, and improving resistance to peeling of the encapsulation material 352 away from the flex cable 300 such as, for example, after several cleaning and autoclave cycles.

Figure 11:
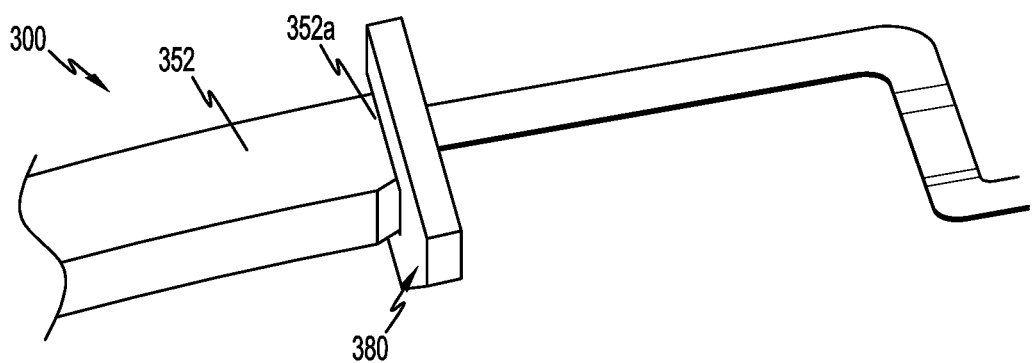
FIG. 11 is a perspective view of an outer edge of the encapsulation material of the flex cable of FIG. 10A, in accordance with another embodiment of the present disclosure.

In embodiments, if further enhanced edge conditions are desired, the outer edges 352a of the encapsulation material 352 may be reinforced. As shown in FIG. 11, a clip 380 may be applied to the outer edges 352a of the encapsulation material 352 after curing to further enhance the bond between the outer edges 352a of the encapsulation material 352 and the flex cable 300. Other clamping devices may be utilized with the encapsulation material such as, for example, a suture wrapped around the outer edges of the encapsulation material or a rigid adhesive applied along the outer edges to reduce or eliminate the flexibility of the outer edges.

As shown in FIGS. 12A and 12B, a rigidizing or stiffening layer 306 may be applied to the flex cable 300 prior to encapsulation to reduce the flexibility of the flex cable 300. The rigidizing layer 306 is disposed on a second side 115 of the substrate 110 of the flex cable 300, which is opposed to the first side 114 of the flex cable 300 including the printed circuit board 122, to support the conductive traces and vias (not explicitly shown). The rigidizing layer 306 minimizes unwanted bending of the conductive traces and vias as bending can compromise (e.g., crack) the conductive traces and vias. In embodiments in which a rigidizing layer 306 is secured to the flex cable 300, the first mold half 360 of the mold 350 would include a deeper channel 361 or the second mold half 370 would include a channel complementary to the channel 361 of the first mold half 360 to accommodate or compensate for the thickness of the rigidizing layer 306. It should be understood that the dimensions of the cavity 351 of the mold 350 correspond with the dimensions (e.g., thickness and width) of the portion of the flex cable 300 being encapsulated.

Figure 13:
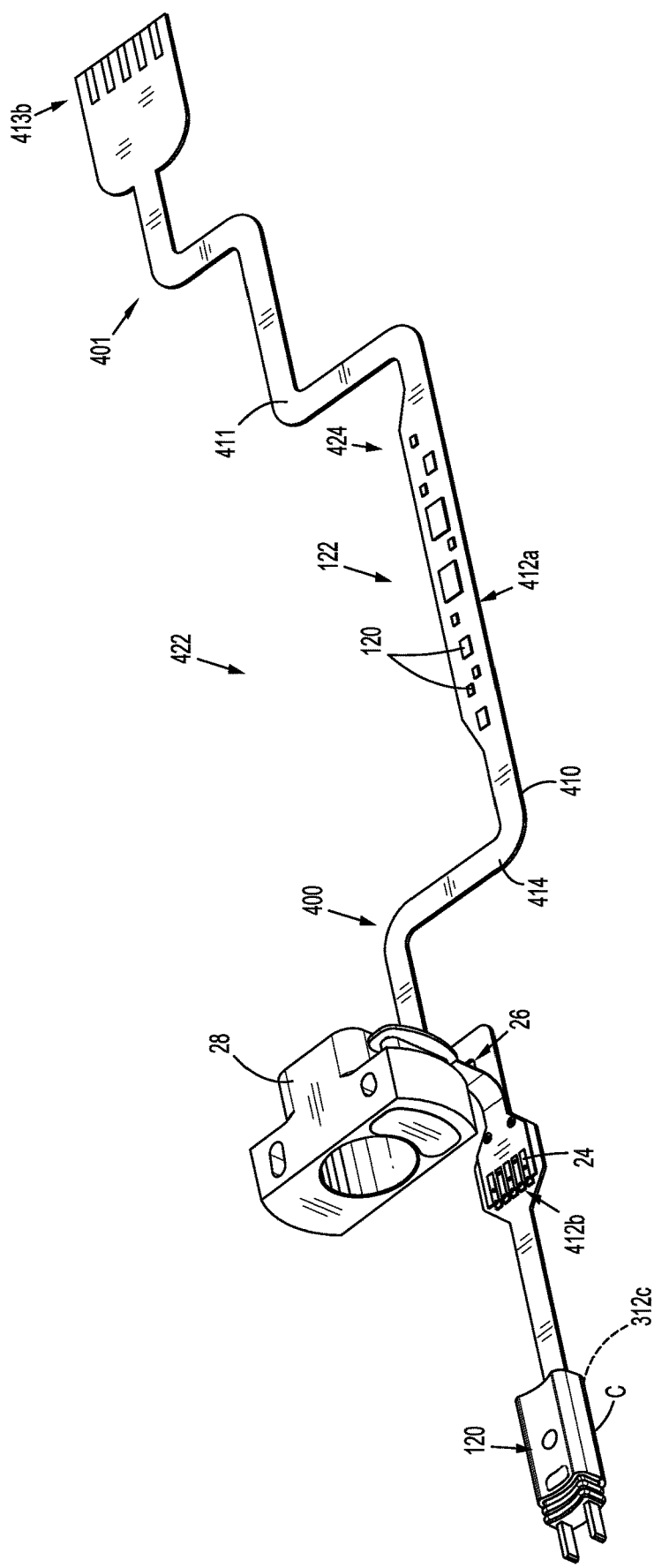
FIG. 13 is a perspective view of a wiring harness of an adapter assembly of the surgical device of FIG. 1, in accordance with another embodiment of the present disclosure.

Turning now to FIG. 13, a wiring harness 422 in accordance with another embodiment of the present disclosure for electronically interconnecting the handle assembly 10 (FIG. 1) and the end effector 30 of the surgical device 1 is shown. The wiring harness 422 is substantially similar to the wiring harness 22 of FIG. 2 and will be described with respect to the differences therebetween. The wiring harness 422 includes a flex cable assembly 424 including first and second flex cables 400, 401. Each of the first and second flex cables 400, 401 includes a body or substrate 410, 411 suitable for supporting and/or electrically connecting electronic components 120 thereto. Each of the substrates 410, 411 is formed from one or more layers or sheets of dielectric material, such as a polymer or a ceramic, and one or more layers of conductive material, such as copper foil, that form conductive traces (not explicitly shown) in the substrate 410, 411, as discussed above with regard to the flex cable 100. Vias (not shown) may interconnect the conductive traces through different layers of the first and second flex cables 400, 401.

Figure 14A:
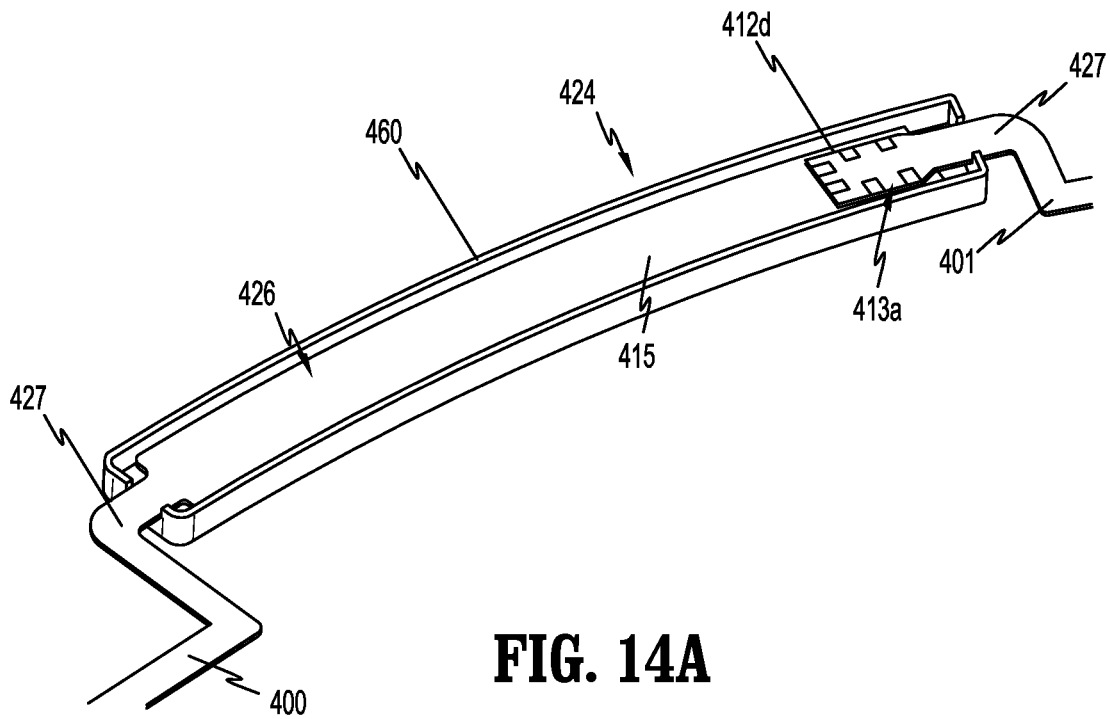
FIG. 14A is a top, perspective view of the wiring harness of FIG. 13 disposed within a first housing half of an encapsulation housing in accordance with an embodiment of the present disclosure.

As shown in FIGS. 13 and 14A, plurality of electrical contact regions 412, 413 (referred to herein as first, second, third, and fourth electrical contact regions 412a-d, and first and second electrical contact regions 413a, 413b) are disposed at terminal ends of the conductive traces (not shown) defined through the substrates 410, 411 of the respective first and second flex cables 400, 401. A first electrical contact region 412a of the first flex cable 400 includes electronic components 120 disposed thereon on a first side 414 of the flex cable 400 that form a printed circuit board 122, and a second electrical contact region 412b is aligned and electrically coupled (e.g., soldered) to an adapter flex cable 26 which, in turn, is electrically coupled to a force sensor 28 positionable within the adapter assembly 20 (FIG. 1). A third electrical contact region 312c (shown in phantom) of the first flex cable 400 is coupled to an electronic component 120 in the form of an electrical connector "C" for electrical connection with the end effector 30 (FIG. 1), and a fourth electrical contact region 412d, disposed on a second side 415 of the flex cable 400, is electrically coupled (e.g., soldered) to a first electrical contact region 413a of the second flex cable 401. The second flex cable 401 further includes a second electrical contact region 413b configured for electrical connection with the handle assembly 10 (FIG. 1).

Figure 14B:
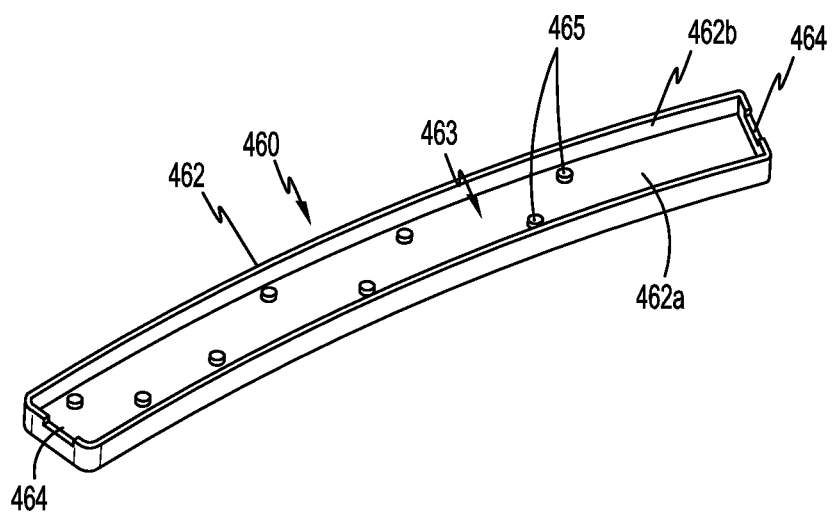
FIG. 14B is a perspective view of the first housing half of the encapsulation housing of FIG. 14A.

With continued reference to FIG. 14A, a printed circuit board portion 426 of the flex cable assembly 424 (e.g., the portion of the flex cable assembly 424 including the printed circuit board 122 of the first flex cable 400 as well as the connection area between the first and second flex cables 400, 401) is positioned within a first housing half 460 of a encapsulation housing 450. As shown in FIGS. 14A and 14B, the first housing half 460 includes a generally u-shaped body 462 including a first or inner surface 462a and a wall 462b extending transversely from the first surface 462a and defining a channel 463 therein. The channel 463 is sized and shaped to receive the printed circuit board portion 426 of the flex cable assembly 424 therein. Cut-outs 464 are defined in side surfaces of the wall 462b of the body 462 for passage of arm portions 427 (e.g., the portions of the first and second flex cables 400, 401 extending away from the printed circuit board portion 426) of the flex cable assembly 424 therethrough. The first surface 462a of the body 462 includes one or more standoffs 465 disposed thereon to space the printed circuit board portion 426 of the flex cable assembly 424 from the first surface 462a of the first housing half 460.

Figure 15:
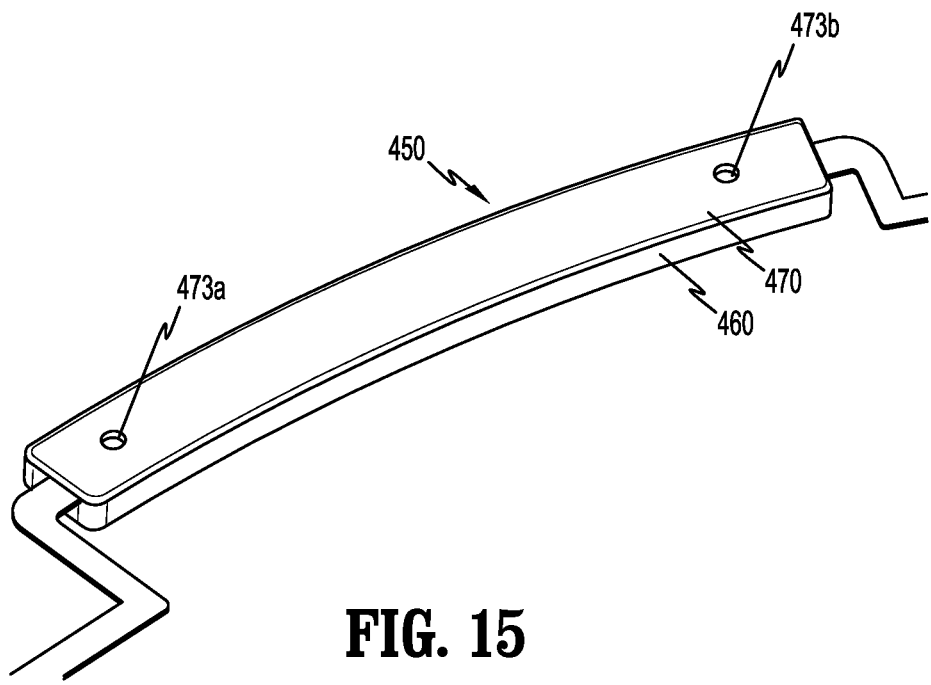
FIG. 15 is a top, perspective view of the encapsulation housing including first and second housing halves.

As shown in FIG. 15, a second housing half 470 of the encapsulation housing 450 is positioned over and secured to the first housing half 460 such that a first or inner surface (not explicitly shown) of the second housing half 470 extends over the channel 463 (FIG. 14B) defined in the first housing half 460 to form a cavity (not explicitly shown) within the encapsulation housing 450. The first and second housing halves 460, 470 may include complementary mechanical structures (e.g., the second housing half 470 may include a rim extending into the channel 463 of the first housing half 460 for frictional engagement therebetween) to align and/or secure the first and second housing halves 460, 470 together. Additionally or alternatively, adhesives or other mating components may be utilized to secure the first and second housing halves 460, 470 together.

The second housing half 470 further includes an inlet opening or sprue 473a and an outlet opening or vent 473b extending through the second housing half 470 and into the cavity of the encapsulation housing 450. The inlet opening 473a allows for passage of an encapsulation material into the cavity of the encapsulation housing 450, and the outlet opening 473b allows for the encapsulation material to vent when the cavity of the encapsulation housing 450 is fully filled with the encapsulation material. The printed circuit board portion 426 of the flex cable assembly 424 is retained within the cavity of the encapsulation housing 450 in spaced relation relative to the first surfaces of the first and second housing halves 460, 470 defining the cavity such that the printed circuit board portion 426 can be fully covered by the encapsulation material.

In a method of encapsulating the printed circuit board portion 426 of the flex cable assembly 424, the flex cable assembly 424 is positioned in the first housing half 460 of the encapsulation housing 450 with the printed circuit board portion 426 positioned within the channel 463 of the first housing half 460 and the arm portions 427 positioned through the cut-outs 464 of the first housing half 460 as shown, for example, in FIGS. 14A-14B. The second housing half 470 is then placed over the first housing half 460 such that the printed circuit board portion 426 of the flex cable assembly 424 is disposed within the encapsulation housing 450 as shown, for example, in FIG. 15. The geometry of the encapsulation housing 450 is optimized to retain the printed circuit board portion 426 of the flex cable assembly 464 in spaced relation relative to the first and second housing halves 460, 470 and the arm portions 427 in a substantially fluid tight relationship between the first and second housing halves 460, 470. After the first and second housing halves 460, 470 are mated, the first and second housing halves 460, 470 may be secured together using, for example, clamps, bands, tape, etc.

The encapsulation material is then injected into the encapsulation housing 450 through the inlet opening 473a until the encapsulation material emerges through the outlet opening 473b indicating that the cavity defined within the encapsulation housing 450 is filled. In embodiments, the encapsulation housing 450 is tilted prior to introducing the encapsulation material into the encapsulation housing 450 so that the inlet opening 473a is lower than the outlet opening 473b to ensure proper and complete filling of the cavity.

Figure 16:
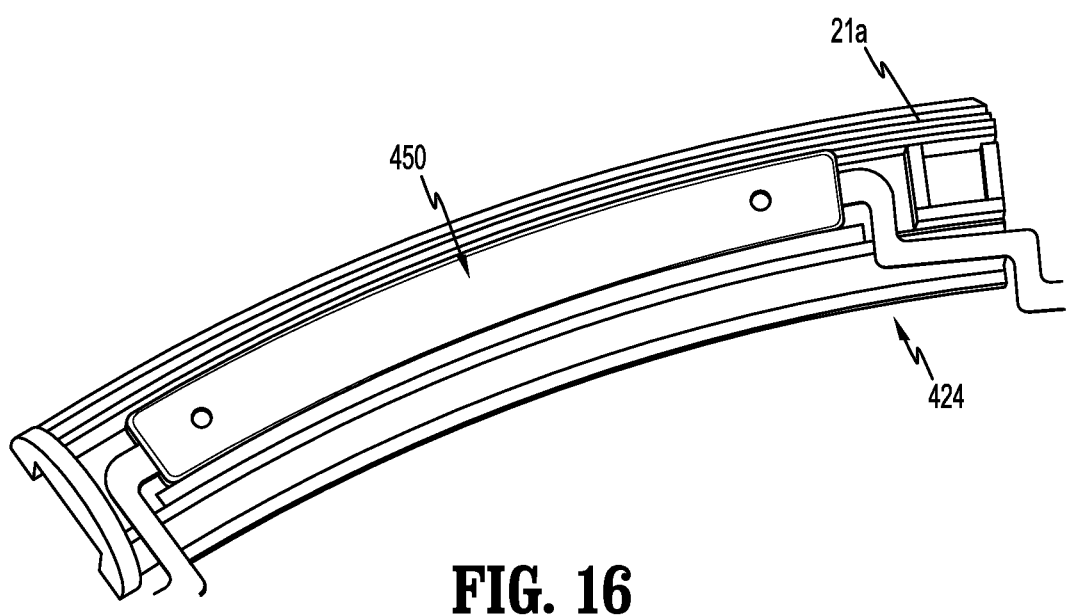
FIG. 16 is a top, perspective view of the flex cable encapsulated within the encapsulation housing of FIG. 15, and coupled to a component of the surgical device of FIG. 1, in accordance with an embodiment of the present disclosure.

Once filling is complete, the encapsulation material is allowed to solidify and/or cure, and the encapsulated flex cable assembly 424 may be assembled or attached to a component of the surgical device, such an inner housing 21a as shown in FIG. 16, which is positioned within the adapter assembly 20 (FIG. 1). Accordingly, the encapsulation housing 450 may be sized and shaped for mating to a desired component of a surgical device and, in some embodiments, the encapsulation housing 450 may include mounting structures or features, such as screw bosses or holes, to allow for mounting to the component. The encapsulation housing 450 may act as a rigidizing layer of the flex cable assembly 424, in addition to fully encapsulating and sealing the printed circuit board 122 and the connection area between the first and second flex cables 400, 401.

With reference now to FIG. 17, the second electrical contact region 413b of the second flex cable 401 of the flex cable assembly 424 may be electrically coupled (e.g., soldered) to a printed circuit board 23 of an electrical assembly 25. The electrical assembly 25 includes a plurality of electrical contact blades 27 supported on the printed circuit board 23 for electrical connection to a pass-through connector (not shown) of the handle assembly 10 (FIG. 1). The printed circuit board 23 has a substrate 23a in the form of an FR4 base and surface mount electrical components 120.

Figure 18C:
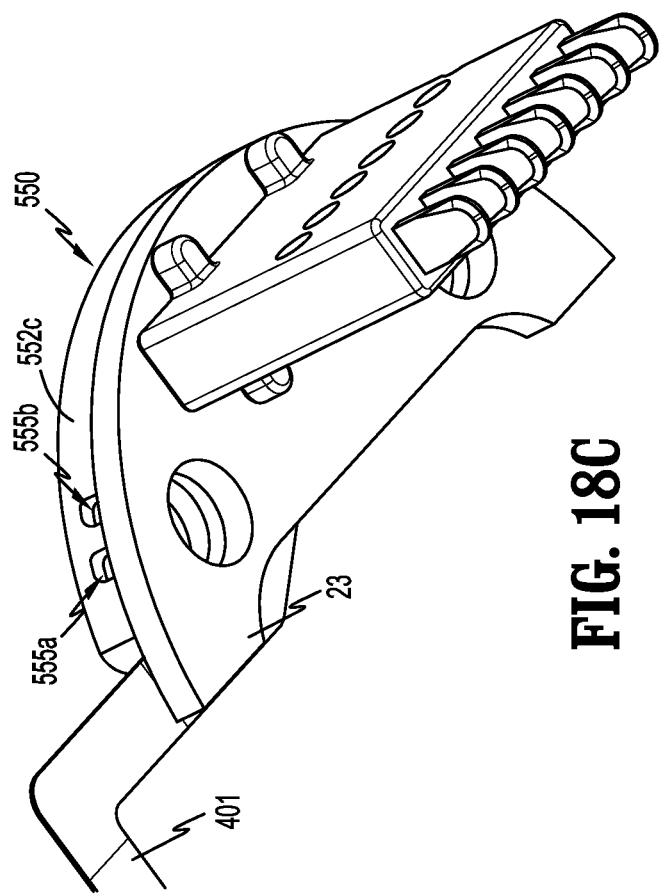

As shown in FIGS. 18A-18C, an encapsulation housing 550 is sized and shaped to mate with the printed circuit board 23 and to cover the electronic components 120 of the printed circuit board 23 as well as the connection area between the second flex cable 401 and the printed circuit board 23. The encapsulation housing 550 includes a generally u-shaped body 552 including a first or inner surface 552a and a wall 552b extending transversely from the first surface 552a and defining a channel 553 therein. The wall 552b is configured to mate with the printed circuit board 23 and the channel 553 is sized and shaped such that the first surface 552a is disposed in spaced relative to the electronic components 120 and the connection area between the printed circuit board 23 and the second flex cable 401 thereby forming a cavity (not explicitly shown) therebetween. The encapsulation housing 550 further includes an inlet opening or sprue 555a and an outlet opening or vent 555b extending through the wall 552b and into the encapsulation housing 550.

In a method of encapsulating the printed circuit board 23 and the connection area between the printed circuit board 23 and the second flex cable 401, after the second electrical contact region 413b is electrically coupled to the printed circuit board 23 (e.g., via a solder connection) as shown in FIG. 17, the encapsulation housing 550 is positioned over the printed circuit board 23 as shown in FIGS. 18A-18C. A fixture (not shown) may be used to secure the encapsulation housing 550 to the printed circuit board 23 (e.g., pins may be positioned through pin openings 556 defined through the encapsulation housing 550 and the printed circuit board 23).

Figure 19:
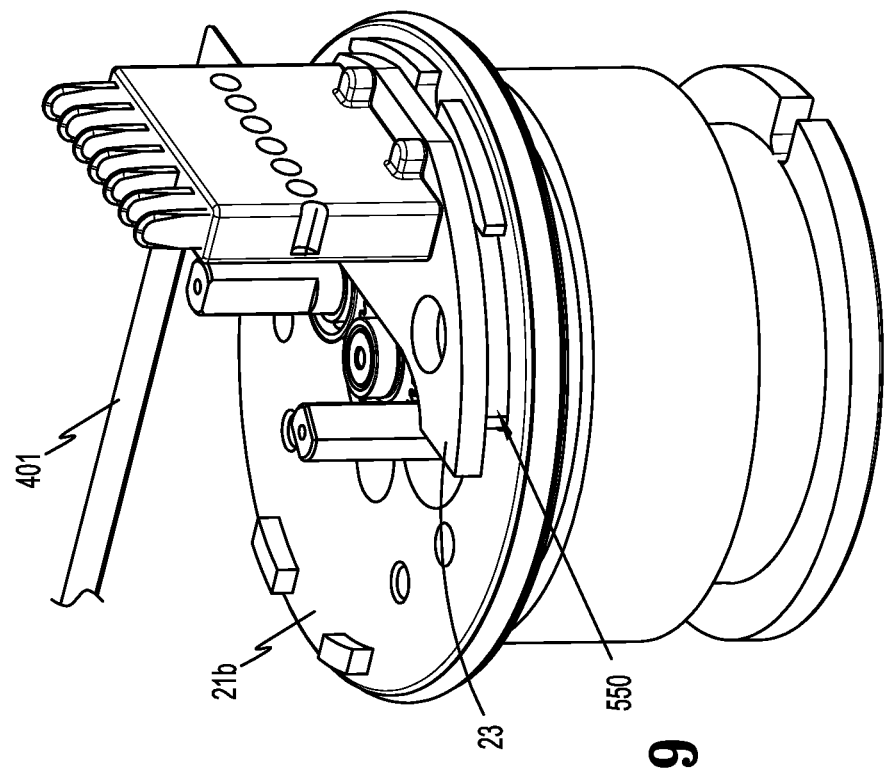
FIG. 19 is a perspective view of the second flex cable and the electrical assembly encapsulated within the encapsulation housing of FIG. 18A, and coupled to a component of the surgical device of FIG. 1 in accordance with an embodiment of the present disclosure.

The encapsulation material is then injected into the cavity of the encapsulation housing 550 through the inlet opening 555a until the encapsulation material emerges through the outlet opening 555b indicating that the encapsulation housing 550 is filled. Once filling is complete, the encapsulation material is allowed to solidify and/or cure, and the encapsulated printed circuit board 23 and second flex cable 401 may be assembled or attached to a component of the surgical device, such a proximal inner housing assembly 21b as shown in FIG. 19, which is positioned within the adapter assembly 20 (FIG. 1). Accordingly, the encapsulation housing 550 may be sized and shaped for mating to a desired component of a surgical device and, in some embodiments, the encapsulation housing 550 may include mounting structures or features, such as screw bosses or holes, to allow for mounting to the component. The encapsulation housing and the encapsulation material cured therein pot the electronic components and the flex cable connection from moisture ingress during, for example, cleaning and sterilization cycles.

It should be understood that while the flex cables are shown and described above as being disposed within an adapter assembly of the surgical device, the flex cables may be utilized in other components of the surgical device, or other surgical devices. It should also be understood that while the flex cables are described and shown disposed within a powered surgical device, the flex cables may be utilized in non-motor driven yet powered surgical devices (e.g., reusable surgical devices subject to washing and/or sterilization procedures).

Persons skilled in the art will understand that the structures specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. For example, the flexible cables of the present disclosure may be utilized in other surgical devices, such as robotic or powered surgical devices/instruments that are subject to sterilization procedures (e.g., autoclaving and/or autowashing). Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

What is claimed is:

1. A method of encapsulating and hermetically sealing a printed circuit board of a flex cable, the method comprising:
   positioning a printed circuit board portion of a flex cable into a channel defined in a first mold half of a mold, the printed circuit board portion including a substrate and electronic components mounted on the substrate;
   mounting a second mold half onto the first mold half to enclose the channel of the first mold half and form a cavity within the mold;
   filling the cavity of the mold with an encapsulation material through an inlet opening defined through the mold; and
   curing the encapsulation material within the cavity of the mold while under vacuum.

2. The method according to claim 1, further comprising positioning arm portions of the flex cable in grooves defined in the first mold half, the grooves extending from opposed sides of the channel.

3. The method according to claim 2, wherein mounting the second mold half onto the first mold half further includes retaining the arm portions under tension between the first and second mold halves such that the printed circuit board portion of the flex cable is disposed in spaced relation relative to inner surfaces of the first and second mold halves defining the cavity of the mold.

4. The method according to claim 3, wherein filling the cavity of the mold further includes completely covering the printed circuit board portion of the flex cable with the encapsulation material.

5. The method according to claim 1, wherein filling the cavity of the mold further includes filling the cavity until the encapsulation material vents through an outlet opening defined through the mold.

6. The method according to claim 1, further comprising:
   opening the mold after the encapsulation material has solidified within the cavity; and
   removing the flex cable from the mold.

7. The method according to claim 6, further comprising clamping outer edges of the encapsulation material to enhance the bond between the encapsulation material and the flex cable.

8. The method according to claim 1, further comprising attaching a rigidizing layer to the substrate of the printed circuit board portion of the flex cable prior to positioning the printed circuit board portion into the channel of the first mold half.

9. A method of encapsulating and hermetically sealing electronic components of a flex cable assembly and integrating the flex cable assembly into a surgical device, comprising:
   positioning a printed circuit board portion of a flex cable assembly into a channel defined in a first housing half of an encapsulation housing, the printed circuit board portion including a substrate of a first flex cable of the flex cable assembly and electronic components mounted on the substrate;
   mounting a second housing half onto the first housing half to enclose the channel of the first housing half and form a cavity within the encapsulation housing;
   filling the cavity of the encapsulation housing with an encapsulation material through an inlet opening defined through the encapsulation housing;
   connecting an electrical contact region of a second flex cable of the flex cable assembly to a rigid printed circuit board;
   positioning a second encapsulation housing over the rigid printed circuit board such that electronic components of the rigid printed circuit board and the electrical contact region of the second flex cable are disposed within a cavity defined between the second encapsulation housing and the rigid printed circuit board; and
   filling the cavity with an encapsulation material through an inlet opening defined through the second encapsulation housing.

10. The method according to claim 9, further comprising positioning arm portions of the flex cable through cut-outs defined in side surfaces of the first housing half of the encapsulation housing.

11. The method according to claim 9, wherein the printed circuit board portion of the flex cable assembly is disposed in spaced relation relative to the inner surfaces of the first and second housing halves defining the cavity of the encapsulation housing and filling the cavity of the encapsulation housing further includes completely covering the printed circuit board portion of the flex cable assembly with the encapsulation material.

12. The method according to claim 11, wherein the inner surface of the first housing half includes standoffs disposed thereon to maintain space between the printed circuit board portion of the flex cable assembly and the inner surface of the first housing half, and positioning the printed circuit board portion into the channel further includes positioning the printed circuit board portion on top of the standoffs.

13. The method according to claim 9, wherein filling the cavity of the encapsulation housing further includes filling the cavity until the encapsulation material vents through an outlet opening defined through the encapsulation housing.

14. The method according to claim 13, further comprising orienting the encapsulation housing so that the inlet opening is lower than the outlet opening prior to filling the cavity with the encapsulation material.

15. The method according to claim 9, further comprising curing the encapsulation material within the encapsulation housing and attaching the encapsulation housing to a component disposed within a surgical device.

16. The method according to claim 15, wherein attaching the encapsulation housing to the component further includes placing the flex cable assembly and the encapsulation housing into an adapter assembly of the surgical device.

17. The method according to claim 9, further comprising curing the encapsulation material within the second encapsulation housing and attaching the second encapsulation housing to a component disposed within a surgical device.

18. A method of encapsulating and hermetically sealing a printed circuit board of a flex cable, the method comprising:
    positioning a printed circuit board portion of a flex cable into a channel defined in a first mold half of a mold, the printed circuit board portion including a substrate and electronic components mounted on the substrate;
    mounting a second mold half onto the first mold half to enclose the channel of the first mold half and form a cavity within the mold;
    filling the cavity of the mold with an encapsulation material through an inlet opening defined through the mold;
    opening the mold after the encapsulation material has solidified within the cavity;
    removing the flex cable from the mold; and
    clamping outer edges of the encapsulation material to enhance the bond between the encapsulation material and the flex cable.

19. A method of encapsulating and hermetically sealing a printed circuit board of a flex cable, the method comprising:
    positioning a printed circuit board portion of a flex cable into a channel defined in a first mold half of a mold, the printed circuit board portion including a substrate and electronic components mounted on the substrate;
    mounting a second mold half onto the first mold half to enclose the channel of the first mold half and form a cavity within the mold;
    filling the cavity of the mold with an encapsulation material through an inlet opening defined through the mold; and
    attaching a rigidizing layer to the substrate of the printed circuit board portion of the flex cable prior to positioning the printed circuit board portion into the channel of the first mold half.

* * * * *